(12) United States Patent
Sanders et al.

(10) Patent No.: US 11,103,651 B2
(45) Date of Patent: Aug. 31, 2021

(54) SAFETY NEEDLE DEVICES

(71) Applicant: Becton, Dickinson and Company, Franklin Lakes, NJ (US)

(72) Inventors: Laurie Sanders, Glen Ridge, NJ (US); Peter Smith, Cary, NC (US); Edward P. Browka, Oneida, NY (US); Eli B. Nichols, Durham, NC (US)

(73) Assignee: Beckon, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/837,748

(22) Filed: Dec. 11, 2017

(65) Prior Publication Data

US 2018/0161515 A1    Jun. 14, 2018

Related U.S. Application Data

(60) Provisional application No. 62/479,507, filed on Mar. 31, 2017, provisional application No. 62/433,294, (Continued)

(51) Int. Cl.
*A61M 5/32* (2006.01)
*A61B 5/15* (2006.01)
(Continued)

(52) U.S. Cl.
CPC ............ *A61M 5/3204* (2013.01); *A61B 5/15* (2013.01); *A61B 5/15003* (2013.01); (Continued)

(58) Field of Classification Search
CPC .............. A61M 5/3271; A61M 5/3243; A61M 5/3272; A61M 5/321; A61M 5/3257; (Continued)

(56) References Cited

U.S. PATENT DOCUMENTS 3,367,488 A    2/1968    Hamilton
3,869,062 A    3/1975    Jaeschke et al.
(Continued)

FOREIGN PATENT DOCUMENTS

CA    2551835 A1    8/2005
CA    2803761 A1    12/2011
(Continued)

OTHER PUBLICATIONS

Final Office Action in U.S. Appl. No. 15/837,018 dated Jun. 18, 2019, 15 pages.
(Continued)

*Primary Examiner* — Nilay J Shah
(74) *Attorney, Agent, or Firm* — Servilla Whitney LLC

(57) ABSTRACT

A safety needle device is disclosed comprising a hub, needle cannula, housing, tether, retractable sleeve, locking member and spring element. The tether is slidably disposed in the housing, the tether having a slot with an enlarged first guide path and a narrowed second guide path extending distally from the enlarged first guide path. The retractable sleeve is configured to move between an initial position, retracted position and an extended position with respect to the housing, wherein the initial position partially exposes a distal tip of the needle cannula, the retracted position fully exposes the needle cannula, and the extended position fully covers the distal tip of the needle cannula.

30 Claims, 25 Drawing Sheets

Related U.S. Application Data filed on Dec. 13, 2016, provisional application No. 62/433,350, filed on Dec. 13, 2016.

(51) Int. Cl.
*A61M 25/06* (2006.01)
*A61B 5/153* (2006.01)

(52) U.S. Cl.
CPC ........ *A61B 5/153* (2013.01); *A61B 5/150022* (2013.01); *A61B 5/150274* (2013.01); *A61B 5/150389* (2013.01); *A61B 5/150496* (2013.01); *A61B 5/150633* (2013.01); *A61B 5/150648* (2013.01); *A61M 5/326* (2013.01); *A61M 5/3243* (2013.01); *A61M 5/3271* (2013.01); *A61M 25/06* (2013.01); *A61M 5/3202* (2013.01); *A61M 5/3257* (2013.01); *A61M 2005/325* (2013.01); *A61M 2005/3247* (2013.01); *A61M 2005/3267* (2013.01)

(58) Field of Classification Search
CPC ........ A61M 5/3202; A61M 2005/3249; A61M 2005/3267; A61B 5/15003; A61B 5/150633; A61B 5/150641; A61B 5/150648; A61B 5/150656
See application file for complete search history.

(56) References Cited

U.S. PATENT DOCUMENTS

| | | |
|---|---|---|
| 4,610,667 A | 9/1986 | Pedicano et al. |
| 4,795,432 A | 1/1989 | Karczmer |
| 4,813,940 A | 3/1989 | Parry |
| 4,911,693 A | 3/1990 | Paris |
| 4,950,250 A | 8/1990 | Haber |
| 5,084,028 A | 1/1992 | Kennedy et al. |
| 5,330,899 A | 7/1994 | Devaughn |
| 5,336,199 A | 8/1994 | Castillo et al. |
| 5,395,347 A | 3/1995 | Blecher |
| 5,415,645 A | 5/1995 | Friend et al. |
| 5,591,138 A | 1/1997 | Vaillancourt |
| 5,688,241 A | 11/1997 | Asbaghi |
| 5,984,899 A | 11/1999 | D'Alessio |
| RE36,885 E | 9/2000 | Blecher |
| 6,884,237 B2 | 4/2005 | Asbaghi |
| 6,926,697 B2 | 8/2005 | Malenchek |
| 7,134,550 B2 | 11/2006 | Groth |
| 7,320,682 B2 | 1/2008 | Cocker et al. |
| 7,361,159 B2 | 4/2008 | Fiser |
| 7,513,888 B2 | 4/2009 | Sircom |
| 7,665,605 B2 | 2/2010 | Erickson et al. |
| 7,811,261 B2 | 10/2010 | Rubinstein |
| 7,871,397 B2 | 1/2011 | Schraga |
| 8,062,265 B2 | 11/2011 | Millerd |
| 8,162,882 B2 | 4/2012 | Rubinstein |
| 8,303,541 B2 | 11/2012 | Chun |
| 8,333,738 B2 | 12/2012 | Millerd |
| 8,439,870 B2 | 5/2013 | Moyer |
| 8,496,627 B2 | 7/2013 | Chelak |
| 8,636,688 B2 | 1/2014 | Shaw |
| 8,636,703 B2 | 1/2014 | Foshee |
| 8,647,307 B2 | 2/2014 | Gratwohl |
| 8,663,129 B2 | 3/2014 | Allen |
| 8,747,355 B2 | 6/2014 | Rubinstein |
| 8,827,961 B2 | 9/2014 | Emmott |
| 8,968,241 B2 | 3/2015 | Liversidge |
| 8,979,794 B2 | 3/2015 | Chevallier |
| 9,050,416 B2 | 6/2015 | Feret |
| 9,061,106 B2 | 6/2015 | Roberts |
| 9,067,024 B2 | 6/2015 | Roberts |
| 9,186,466 B2 | 11/2015 | Zachek |
| 9,352,099 B2 | 5/2016 | Roberts |
| 9,352,100 B2 | 5/2016 | Ward |
| 9,352,101 B2 | 5/2016 | Roberts |
| 9,370,327 B2 | 6/2016 | Teoh |
| 9,408,632 B2 | 8/2016 | Erskine |
| 9,445,760 B2 | 9/2016 | Allen |
| 9,694,140 B2 | 7/2017 | Rubinstein |
| 9,848,810 B2 | 12/2017 | Allen |
| 2001/0031949 A1* | 10/2001 | Asbaghi ................ A61M 5/326 604/198 |
| 2002/0063074 A1 | 5/2002 | Simm et al. |
| 2002/0165497 A1 | 11/2002 | Greene |
| 2003/0093009 A1 | 5/2003 | Newby et al. |
| 2003/0120209 A1* | 6/2003 | Jensen ................ A61M 5/326 604/110 |
| 2003/0121815 A1 | 7/2003 | Bergeron et al. |
| 2003/0181867 A1* | 9/2003 | Bressler ............ A61M 25/0625 604/263 |
| 2003/0181869 A1 | 9/2003 | Swenson et al. |
| 2005/0067309 A1 | 3/2005 | Choi |
| 2005/0113750 A1 | 5/2005 | Targell |
| 2005/0119627 A1 | 6/2005 | Crawford |
| 2005/0279664 A1 | 12/2005 | Hommann |
| 2006/0189933 A1 | 8/2006 | Alheidt et al. |
| 2006/0189934 A1 | 8/2006 | Kuracina et al. |
| 2006/0213793 A1 | 9/2006 | Brand |
| 2006/0264828 A1 | 11/2006 | Woehr et al. |
| 2009/0024093 A1 | 1/2009 | Carrel et al. |
| 2009/0254042 A1* | 10/2009 | Gratwohl ............ A61M 5/326 604/198 |
| 2009/0299295 A1 | 12/2009 | Rubinstein et al. |
| 2010/0029877 A1 | 11/2010 | Rubinstein |
| 2011/0288491 A1 | 11/2011 | Newman et al. |
| 2011/0319817 A1 | 12/2011 | Rubinstein et al. |
| 2012/0029440 A1 | 2/2012 | Boyd et al. |
| 2012/0059331 A1 | 3/2012 | Dibiasi et al. |
| 2012/0130342 A1 | 5/2012 | Cleathero |
| 2014/0022877 A1 | 1/2014 | Ward |
| 2014/0048433 A1 | 2/2014 | Dasbach et al. |
| 2014/0097111 A1 | 4/2014 | Dasbach et al. |
| 2014/0013570 A1 | 5/2014 | Rubinstein |
| 2014/0036480 A1 | 12/2014 | Rubinstein |
| 2015/0034516 A1 | 2/2015 | Chapin et al. |
| 2015/0094659 A1 | 4/2015 | Schraga |
| 2015/0165132 A1 | 6/2015 | Perot et al. |
| 2015/0019058 A1 | 7/2015 | Imai |
| 2015/0182704 A1 | 7/2015 | Chevallier |
| 2015/0297837 A1 | 10/2015 | Schraga |
| 2015/0297881 A1 | 10/2015 | Sanders et al. |
| 2016/0074572 A1 | 3/2016 | Spool et al. |
| 2016/0303331 A1 | 10/2016 | Evans et al. |
| 2017/0106136 A1 | 4/2017 | Dibiasi |
| 2017/0233168 A1 | 8/2017 | Horvath et al. |
| 2018/0161490 A1 | 6/2018 | Sanders et al. |
| 2018/0161492 A1 | 6/2018 | Sanders et al. |
| 2018/0161521 A1 | 6/2018 | Sanders et al. |

FOREIGN PATENT DOCUMENTS

| | | | |
|---|---|---|---|
| CN | 103079610 | A | 5/2013 |
| EP | 0734739 | A2 | 10/1996 |
| EP | 0750915 | A2 | 1/1997 |
| EP | 1537890 | A1 | 6/2005 |
| EP | 1949928 | A1 | 7/2008 |
| EP | 2585146 | B1 | 3/2017 |
| FR | 2884723 | A1 | 10/2006 |
| FR | 2930160 | A1 | 10/2009 |
| JP | 2007519474 | A | 7/2007 |
| JP | 2012500063 | A | 1/2012 |
| JP | 2013529973 | A | 7/2013 |
| MX | 2013/000081 | A | 3/2013 |
| MX | 349289 | B | 7/2017 |
| WO | 92/06725 | A1 | 4/1992 |
| WO | 2008050158 | A2 | 5/2008 |
| WO | 2009040602 | A1 | 4/2009 |
| WO | 2009/114777 | A1 | 9/2009 |
| WO | 2010/033767 | A2 | 3/2010 |
| WO | 2012/000833 | A1 | 1/2012 |
| WO | 2012/013587 | A1 | 2/2012 |

(56) References Cited

FOREIGN PATENT DOCUMENTS

| WO | 2013073122 A1 | 5/2013 |
| WO | 2015/164416 A1 | 10/2015 |
| WO | 2016/087187 A1 | 6/2016 |

OTHER PUBLICATIONS

Non-Final Office Action in U.S. Appl. No. 15/837,008 dated Jul. 25, 2019, 23 pages.
PCT International Search Report and Written Opinion in PCT/US2017/065693 dated Mar. 7, 2018, 12 pages.
PCT International Search Report and Written Opinion in PCT/US2017/065716 dated Mar. 21, 2018, 14 pages.
PCT International Search Report and Written Opinion in PCT/US2017/065717 dated Mar. 19, 2018, 12 pages.
PCT International Search Report and Written Opinion in PCT/US2017/065692 dated Mar. 13, 2018, 14 pages.
PCT International Preliminary Report on Patentability in PCT/US2017/065688 dated Jun. 27, 2019, 9 pages.
PCT International Preliminary Report on Patentability in PCT/US2017/065689 dated Jun. 27, 2019, 10 pages.
PCT International Preliminary Report on Patentability in PCT/US2017/065692 dated Jun. 27, 2019, 8 pages.
PCT International Preliminary Report on Patentability in PCT/US2017/065693 dated Jun. 27, 2019, 7 pages.
PCT International Preliminary Report on Patentability in PCT/US2017/065716 dated Jun. 27, 2019, 9 pages.
PCT International Preliminary Report on Patentability in PCT/US2017/065717 dated Jun. 27, 2019, 9 pages.
PCT International Preliminary Report on Patentability in PCT/US2017/065718 dated Jun. 27, 2019, 12 pages.
PCT International Search Report and Written Opinion in PCT/US2017/065718 dated Jan. 2, 2019, 18 pgs.
PCT Invitation to Pay Additional Fees, and, Where Applicable, Protest Fee in PCT/US2017/065718 dated Apr. 9, 2018, 13 pages.
PCT International Search Report and Written Opinion in PCT/US2017/065688 dated Feb. 26, 2018, 13 pages.
PCT Invitation to Pay Additional Fees, and, Where Applicable, Protest Fee dated Feb. 20, 2018, 12 pages.
Final Office Action in U.S. Appl. No. 15/837,756 dated Feb. 28, 2020, 34 pages.
Final Office Action in U.S. Appl. No. 15/837,810 dated Feb. 28, 2020, 24 pages.
Non-Final Office Action in U.S. Appl. No. 15/837,020 dated Feb. 3, 2020, 11 pages.
Non-Final Office Action in U.S. Appl. No. 15/837,011 dated Oct. 7, 2019, 8 pages.
Non-Final Office Action in U.S. Appl. No. 15/837,756 dated Oct. 17, 2019, 39 pages.
Non-Final Office Action in U.S. Appl. No. 15/837,810 dated Oct. 17, 2019, 27 pages.
Non-Final Office Action in U.S. Appl. No. 15/837,018 dated Dec. 5, 2019, 14 pages.
PCT International Search Report and Written Opinion in PCT/US2021/019381 dated Jun. 11, 2021, 18 pages.

\* cited by examiner

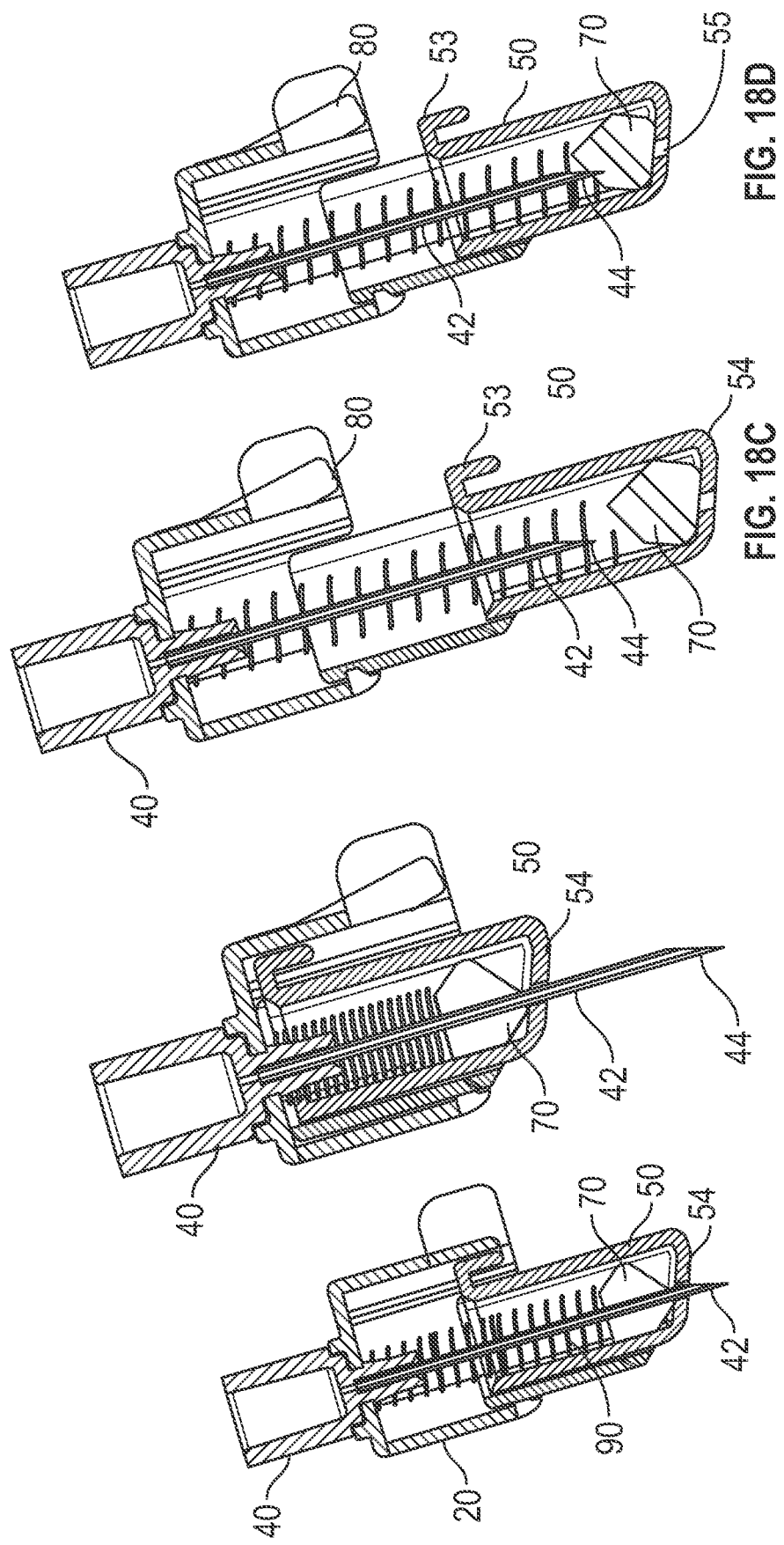

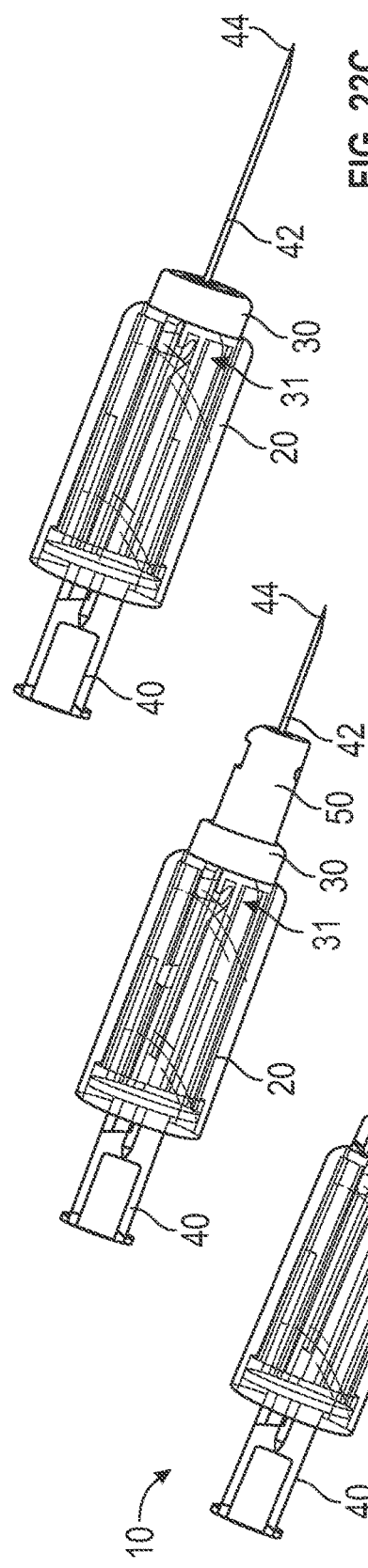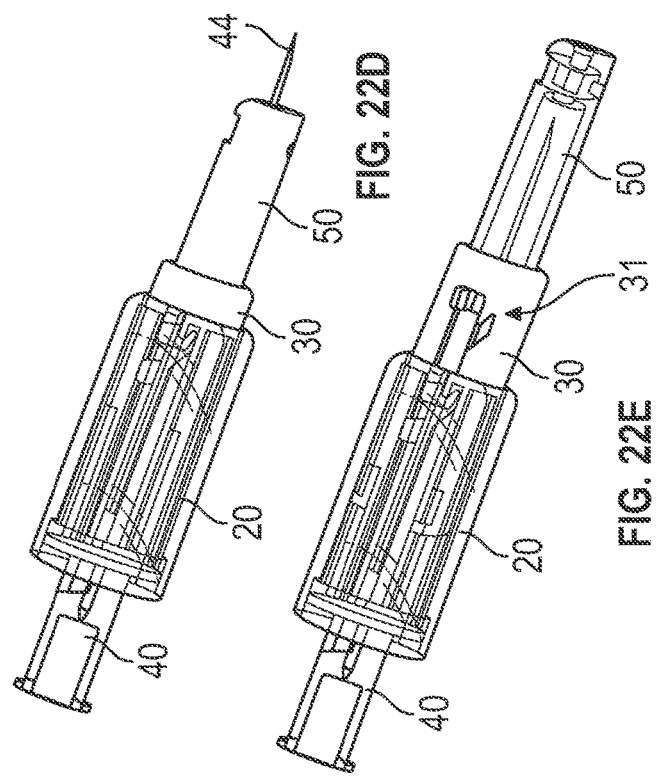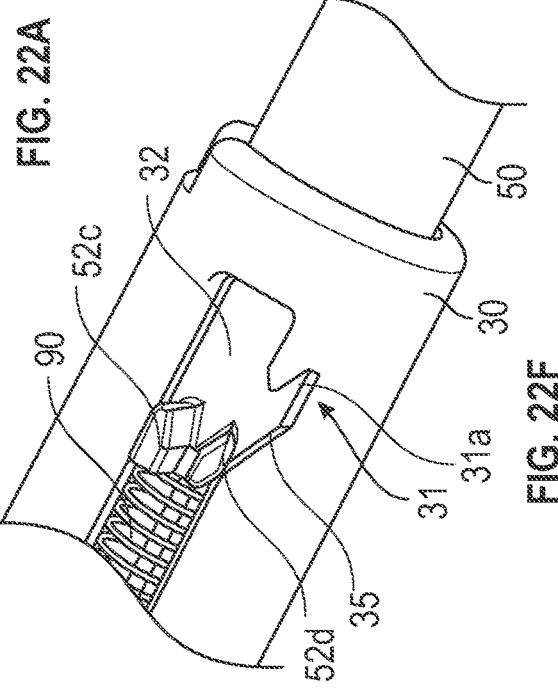

SAFETY NEEDLE DEVICES

CROSS-REFERENCE TO RELATED APPLICATIONS

This application claims priority under 35 U.S.C. § 119(e) to U.S. Provisional Application No. 62/433,294, filed Dec. 13, 2016, U.S. Provisional Application No. 62/433,350, filed Dec. 13, 2016 and U.S. Provisional Application No. 62/479,507, filed Mar. 31, 2017, the disclosures of which are incorporated herein by reference in their entirety.

TECHNICAL FIELD

The present disclosure relates generally to a safety needle device, and more particularly, in specific embodiments, to a single-use passive safety needle device.

BACKGROUND

Needle devices are used throughout the medical industry for the injection and withdrawal of a wide variety of fluids and solutions into and from the human body. Because of the numerous potential hazards associated with the handling and manipulation of bodily fluids, and particularly blood, there are a number of known safety features that are frequently incorporated into various types of needle devices to protect the practitioner from accidental exposure to the needle.

Prior safety needle devices include various disadvantages including a retractable sleeve which requires one or more of long stroke distances to activate the safety feature, multi-component retraction and locking elements, and creation of an undesirable significant force against a patient's skin during activation of the safety feature upon receiving an injection. In addition, conventional retraction syringe assemblies often do not incorporate reuse prevention features, and thus, the retraction mechanism of the syringe may be reset so the syringe barrel may be reused. The reuse of syringe assemblies without sterilization or sufficient sterilization is believed to facilitate the transfer of contagious diseases. Further, the retraction features of conventional syringes may also require the user to actively activate the retraction mechanism. Accordingly, the chance of human error in failure to activate or properly activate the retraction mechanism can lead to continued exposure of needles leading to needle stick injuries.

Existing retracting sleeve safety needle devices also may include a single-use safety needle device assembly that obscures a substantial majority or an entirety of an injection needle from view before, during, and after an injection procedure. However, many injection procedures require that the practitioner know precisely the location and depth to which the needle is inserted in the patient's tissue to be sure that medication is delivered to an appropriate location. In addition, many users falsely assume that they were "safe" from needle stick injuries, even when the safety needle devices are in the non-locked initial state, due to the tip of the prior art retracting sleeve safety needle devices being fully covered in an unlocked state.

Thus, there is a need to provide a safety needle device having an activation mechanism, for example, a passive activation mechanism, which overcomes one or more of the deficiencies of existing retractable sleeve safety needle devices. It may also be desirable to provide a safety needle advice that can provide one or more of activation over a shorter stoke distance, ease of use, increased patient comfort, low part count, minimal part complexity, relatively compact design and relatively short overall length, minimal to no sleeve rotation against a patient's skin, and clear and unobstructed view of the needle in an initial position prior to injection into a patient.

SUMMARY

One aspect of the present disclosure pertains to a safety needle device. Specific embodiments pertain to a single-use passive safety needle device. A first embodiment of a safety needle device comprises a hub configured to couple to a syringe, a needle cannula having a proximal end attached to the hub and distal tip. The first embodiment of the safety needle device also includes a housing having a proximal end, a distal end, and a housing body. The hub is disposed on the proximal end of the housing. The first embodiment safety needle device also includes a tether movably (e.g., slidably) disposed in the housing, the tether having a slot with an enlarged first guide path and a narrowed second guide path extending distally from the enlarged first guide path. The first embodiment further includes a retractable sleeve slidably disposed in the tether, the retractable sleeve having one or more protrusions to slidably engage the slot, the retractable sleeve configured to move between an initial position, a retracted position and an extended position with respect to the housing, wherein the initial position partially exposes a distal tip of the needle cannula, the retracted position fully exposes the needle cannula, and the extended position fully covers the distal tip of the needle cannula. The first embodiment of the safety needle device also includes a locking member disposed in the retractable sleeve, the locking member configured to cover the distal tip of the needle cannula when retractable sleeve is in the extended position. The first embodiment of the safety needle device also includes a spring element to bias the retractable sleeve from the retracted position to the extended position. In specific embodiments, the first embodiment is a single-use passive safety needle device.

In one or more embodiments, movement (e.g., proximal movement) of the retractable sleeve from the initial position causes the one or more protrusions of the retractable sleeve to rotate the tether and move the one or more protrusions to move from from the enlarged first guide path on the tether to the narrowed second guide path on the tether. In one or more embodiments, the tether rotates with respect to the housing during proximal movement of the retractable sleeve from the initial position. Rotation of the tether from the initial position to the second position guides the one or more protrusions of the retractable sleeve from the enlarged first guide path of the tether to the narrowed second guide path of the tether. In some embodiments, the one or more protrusions move from the enlarged first guide path, contact a ramping surface and then move to the narrowed second guide path.

In one or more embodiments, the tether comprises a first end attached to the housing body and a second end attached to the retractable sleeve. In one or more embodiments, the tether extends from the housing as the retractable sleeve is moved distally along a length of the cannula.

In one or more embodiments, the enlarged first guide path of the tether intersects the narrowed second guide path of the tether. In one or more embodiments, the narrowed second guide path is generally parallel to a central axis and extends along the tether body. In one or more embodiments, the enlarged first guide path may comprise an angle, curvature or taper relative to a central axis. The angle, curvature or taper of the first guide path may allow the one or more protrusions to rotate the tether from the first guide path to the second guide path.

In one or more embodiments, the one or more protrusions may comprise a first protrusion of a first length "L1" and a second protrusion having a second length less than "L2". In one or more embodiments, the first protrusion may be adjacent to the second protrusion. In another embodiment, the first protrusion may be located 90° to the second protrusion. In yet another embodiment, the first protrusion may be located 180° to the second protrusion. In one or more embodiments, the first protrusion is T-shaped.

In one or more embodiments, movement of the retractable sleeve from the retracted position to the extended position engages the locking member to a distal tip of the needle cannula.

In one or more embodiments, the locking member inhibits reuse of the passive safety needle device by inhibiting translation of the retractable sleeve.

In one or more embodiments, the locking member may comprise a metal latch. In another embodiment, the locking member may comprise a gate.

The spring element biases the retractable sleeve from the retracted position to the extended position. In one or more embodiments, the spring element is a coil spring.

In one or more embodiments, the one or more protrusions comprise a protrusion radially extending from a proximal portion of the retractable sleeve.

In another embodiment, the one or more protrusions comprise a first protrusion radially extending from a proximal portion of the retractable sleeve and having a height and a second protrusion radially extending from a proximal portion of the retractable sleeve and having a height, the height of the first protrusion being greater than the height of the second protrusion. In yet another embodiment, the one or more protrusions comprise a single radially extending protrusion having a first portion having a first height and a second portion extending laterally from the first portion, the second portion having a second height that is less than the first height. In one or more embodiments, the second protrusion contacts the first slot when the retractable sleeve is in the initial position and rotates the tether when the retractable sleeve is moved toward the second position.

In one or more embodiments, the slot in the tether may include a transition region between the enlarged first guide path and the narrowed second guide path, the transition region including an angled surface that uses the one or more protrusions to rotate the tether to the narrowed second guide path from the enlarged first guide path.

In one or more embodiments, the enlarged first guide path may comprise a branch defining a hook-shaped portion that engages the one or more protrusions and prevents relative rotation of the tether and the sleeve. The one or more protrusions may comprise a single radially extending protrusion having a first portion having a first height and a second portion extending laterally from the first portion, the second portion may have a second height that is less than the first height, and the second portion may have a surface that nests in the hook-shaped portion.

BRIEF DESCRIPTION OF THE DRAWINGS

FIG. 18A illustrates a cross-sectional view of a safety needle device of FIG. 16 with the sheath in an initial position;

FIG. 18B illustrates a cross-sectional view of a safety needle device of FIG. 16 with the sleeve in a retracted position;

FIG. 18C illustrates a cross-sectional view of a safety needle device of FIG. 16 with the sleeve in an extended position;

FIG. 18D illustrates a cross-sectional view of a safety needle device of FIG. 16 with the sleeve in an extended and locked position;

FIG. 22A illustrates a perspective view of a safety needle device according to an alternate embodiment having a tether including a hook with the sleeve in an initial position;

FIG. 22B illustrates a perspective view of the safety needle of FIG. 22A with the sleeve in a partially retracted position;

FIG. 22C illustrates a perspective view of the safety needle device of FIG. 22A with the sleeve in a fully retracted position;

FIG. 22D illustrates a perspective view of the safety needle device of FIG. 22A with the sleeve in partially extended position;

FIG. 22E illustrates a perspective view of the safety needle device of FIG. 22A with the sleeve in a fully extended and locked position;

FIG. 22F illustrates an enlarged perspective view of a portion of the safety needle device of FIG. 22A;

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

With respect to terms used in this disclosure, the following definitions are provided.

As used herein, the use of "a," "an," and "the" includes the singular and plural.

In this disclosure, a convention is followed wherein the distal end of the device is the end closest to a patient and the proximal end of the device is the end away from the patient and closest to a practitioner.

As used herein, a "safety needle device" refers to a device having a needle suitable for injection that includes one or more features to prevent needle stick injuries. As used herein, a "passive safety needle device" refers to a safety needle device with a passive activation mechanism that has a sheath or sleeve that automatically covers the distal end of the needle after a patient has been injected. Thus, "passive" refers to the fact that the needle distal tip is shielded by a sleeve or sheath automatically after the needle cannula is removed from a subject or patient. A practitioner or user of the device does not have to activate the sleeve or sheath by pressing a button, twisting the device or taking any other action.

Reference to "syringe" includes syringes that are indicated for use with needles, nozzle, tubing, or for use in flush systems. As used herein, the term "syringe" refers to a simple pump-like device consisting of a plunger rod that fits tightly in a barrel or tube. The plunger rod can be pulled or pushed along inside the barrel, allowing the syringe to take in and expel a liquid or gas through an opening at the open end of the barrel. The open end of the syringe may be fitted with a needle, nozzle, or tubing to help direct the flow of fluid into and out of the barrel. The syringe may be sterile or unsterile, depending upon the needs of the technician.

One or more embodiments of the safety needle device of the present disclosure provide a safety needle device with a passive activation mechanism. In one or more embodiments, a device is provided that allows for at least one of shorter distance for lockout travel, ease of use, increased patient comfort, low part count, minimal part complexity, relatively compact design, and clear and unobstructed view of needle in an initial position.

Figure 1:
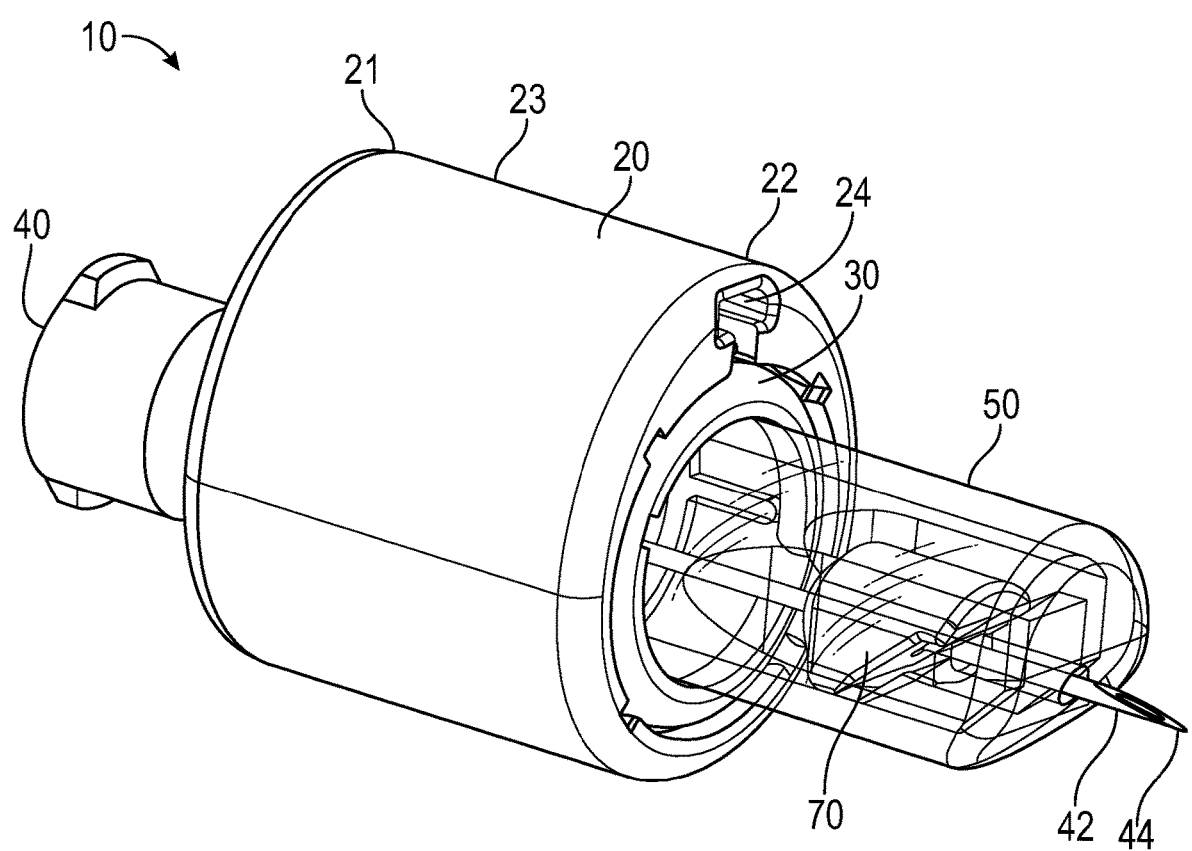
FIG. 1 illustrates a perspective view of a safety needle device according to a first embodiment.

FIG. 1 illustrates a safety needle device 10 that may be removably coupled to a standard or specially configured syringe (not shown). Although the illustrated safety needle device 10 is configured to be coupled to and removed from a syringe, the safety needle device 10 may instead be integrally formed with the syringe. The syringe is generally of a known type suitable for the withdrawal and injection and/or aspiration of fluids or other solutions by way of the safety needle device 10.

FIGS. 1-4 illustrate a first exemplary embodiment of a safety needle device 10 according to the present disclosure. As shown in FIG. 1, safety needle device 10 includes a hub 40 configured to couple to a syringe (not shown), a needle cannula 42 having a proximal end 43 attached to the hub 40 and distal tip 44. The safety needle device 10 also includes a housing 20 having a proximal end 21, a distal end 22, a housing body 23 and an opening 24 located on the distal end. The hub is disposed on the proximal end of the housing. Housing 20 may be of a unitary construction or may be formed from a plurality of components. In one or more embodiments, a proximal end 21 and a distal end 22 of the housing 20 can be separate components that are joined using techniques, such as but not limited to sonic welding, adhesive, snap or press fitting, or the like.

In one or more embodiments, the proximal end 21 of the housing 20 may be connectable to a luer connection or other fluid connector via hub 40. As shown in FIG. 1, needle cannula 42 may be connected to hub 40 disposed at the proximal end 21 of the housing 20. In one or more embodiments, needle cannula 42 may have a beveled tip at the distal tip 44, as shown in FIG. 1. Needle cannula 42 is disposed in the hub 40 in a manner as would be well understood in the art. Hub 40 may be integrally formed with the proximal end 21 of housing 20. Hub 40 may be configured to be removable or permanently attached to a syringe, or alternatively, hub 40 may be integrally formed with a syringe. For example, hub 40 may include internal or external threads or other suitable coupling, latching, or locking features such as tabs, slots, projections, pressure/snap fits, and the like, for removably coupling the safety needle device to a syringe. In some embodiments, the housing may include a needle support 41 that extends axially from the hub 40 to support the needle cannula 42. Hub 40 is in fluid communication with the needle cannula 42 to permit fluid to pass between a syringe and the needle cannula 42.

The needle cannula 42 extends from the hub 40 disposed in the housing 20 and extends to a distal tip 44. As shown in FIG. 1, distal tip 44 of the needle cannula 42 is partially exposed and protruding from the distal end of the retractable sleeve 50 so as to be visible when the retractable sleeve 50 is in an initial position. The shaft of the needle cannula 42 is exposed from the retractable sleeve 50 when the retractable sleeve 50 is in a retracted position.

Needle cannula 42 in accordance with the present disclosure can be formed from conventional materials such as steel or more preferably stainless steel. It will be realized by the skilled artisan that medical grade plastics, composites, ceramics, or like materials can be substituted.

Figure 2:
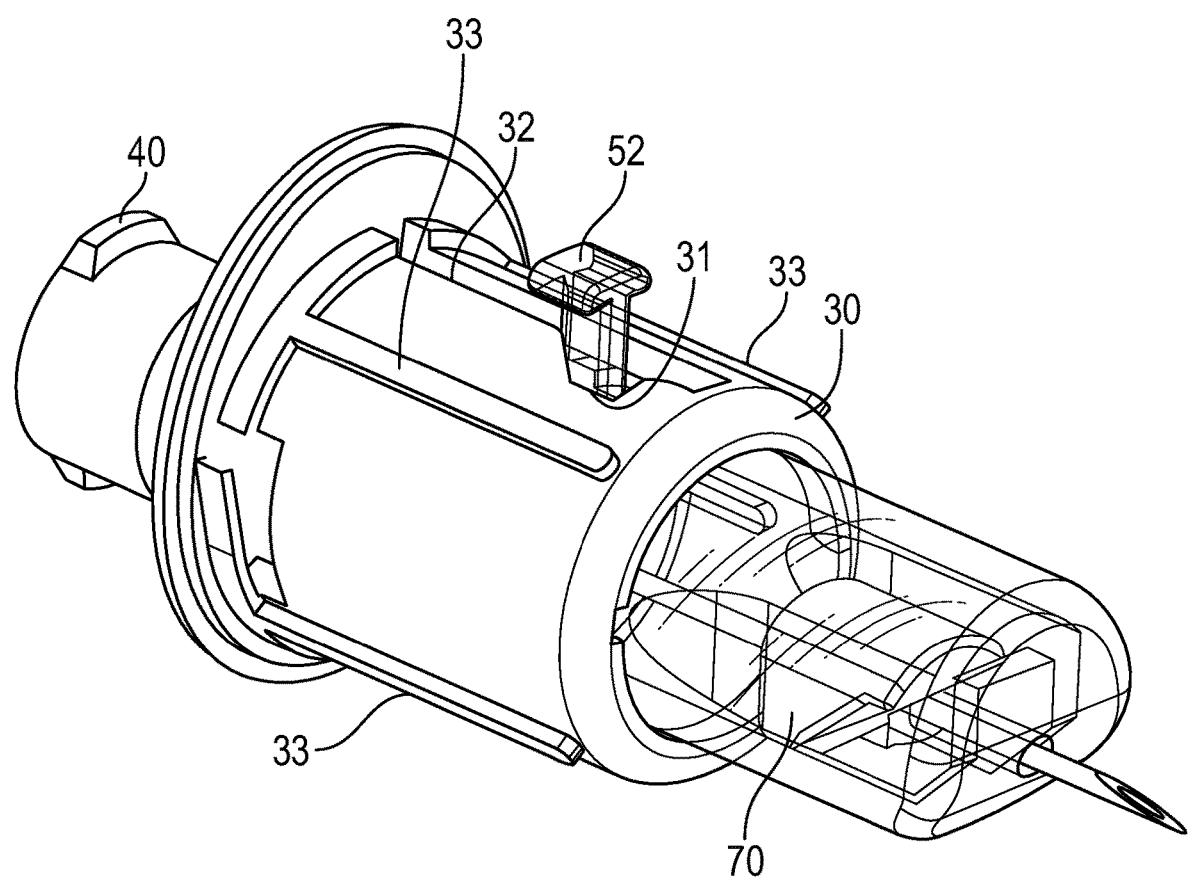
FIG. 2 illustrates a perspective view of a safety needle device shown in FIG. 1 in an initial state and without a housing.

In one more embodiments, incorporation of the tether 30 allows the overall size (length from the proximal end to the distal end) of the safety needle device to be significantly reduced. In one or more embodiments, as shown in FIG. 2, tether may be a telescoping tether having a first end attached to the housing body 23 and a second end attached to retractable sleeve 50. In one or more embodiments, tether 30 extends to form an enclosure around the needle cannula as retractable sleeve 50 is moved distally along a length of the cannula.

The tether 30 is slidably disposed in the housing 20. Tether 30 is generally parallel to a central axis which extends along the housing body 23. In one or more embodiments, tether 30 has a slot with an enlarged first guide path 31 with a proximal angled lead ramp, a ledge at the distal end of the enlarged first guide path for seating one or more protrusions 52 of retractable sleeve 50, and a narrowed second guide path 32 extending distally from the enlarged first guide path 31. First guide path 31 is positioned at an angle, curvature or taper relative to the axis and intersects the second guide path 32. Second guide path 32 is generally parallel to a central axis which extends along the housing body 23. In one or more embodiments, the angle, curvature or taper of the first guide path 31 permits the one or more protrusions 52 to shift between the first guide path 31 and second guide path 32. In one or more embodiments, the slot in the tether may include a transition region between the enlarged first guide path and the narrowed second guide path, the transition region including an angled surface or ramped surface 31a that uses the one or more protrusions to rotate the tether to the narrowed second guide path from the enlarged first guide path.

In one or more embodiments, the first guide path 31, and the second guide path 32 are disposed on the inner diameter of the tether 30 to prevent tampering or contact from a user.

The tether 30, having a proximal end 30a and a distal end 30b, may have the proximal end connected to housing 20 or hub 40 and the distal end of the tether may be connected to the retractable sleeve 50. In one or more embodiments, tether 30 may be in the form of a tube or concentric cone-shaped enclosures. The tether 30 deploys in the form of a tube or cone-shaped enclosure around the needle cannula 42. Tether 30 extends to form an enclosure around the cannula as retractable sleeve is moved distally along the length of the cannula.

The term "retractable sleeve" is intended to include any sort of tubular member. The retractable sleeve 50 is dimensioned to be compatible with the size and type of needle cannula 40 as will be appreciated by those skilled in the art. The housing 20 includes a housing body 23 with an internal hollow region in which the retractable sleeve 50 may move in the proximal and distal direction. Retractable sleeve 50 may be configured to move between an initial position, a retracted position and an extended position with respect to housing 20, wherein the initial position partially exposes a distal tip 44 of the needle cannula 42, the retracted position fully exposes the needle cannula 42, and the extended position fully covers the distal tip 44 of the needle cannula 42. The safety needle device also includes a locking member 70 disposed in the retractable sleeve 50, the locking member being configured to cover the distal tip of the needle cannula when retractable sleeve is in the extended position. The safety needle device also includes a spring element 90 to bias the retractable sleeve 50 from the retracted position to the extended position.

In one or more embodiments, retractable sleeve 50 is slidably disposed in the tether 30, the retractable sleeve having one or more protrusions 52 to slidably engage the slot of the tether. The distal end of the retractable sleeve includes an aperture in a distal wall thereof, through which distal tip 44 of cannula 42 is exposed. As the retractable sleeve 50 moves distally along the needle cannula 42, the tether 30 rotates and extends to the length of the needle cannula 42.

Tether 30 and retractable sleeve 50 are designed to telescopically slide with respect to each other, but not to extend past each other, and the total extension length of the tether 30 is long enough to permit the retractable sleeve 50 to cover the length of needle cannula and for locking member 70 to extend over and cover the sharp distal tip 44 of the needle cannula 42. Tether 30 is configured to fully cover needle cannula 42 when the retractable sleeve is maximally extended to cover and shield the sharp distal tip 44 of the needle cannula.

Figure 3:
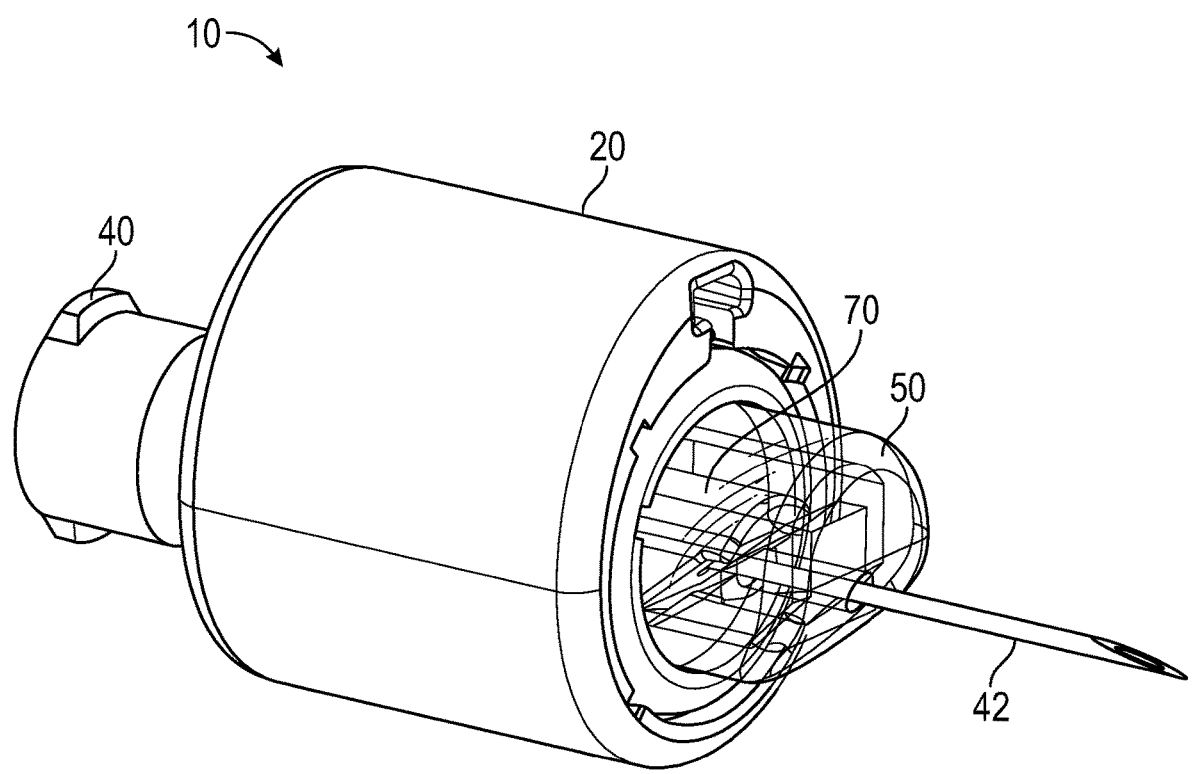
FIG. 3 illustrates a perspective view of a safety needle device shown in FIG. 1 in a retracted state.
Figure 4:
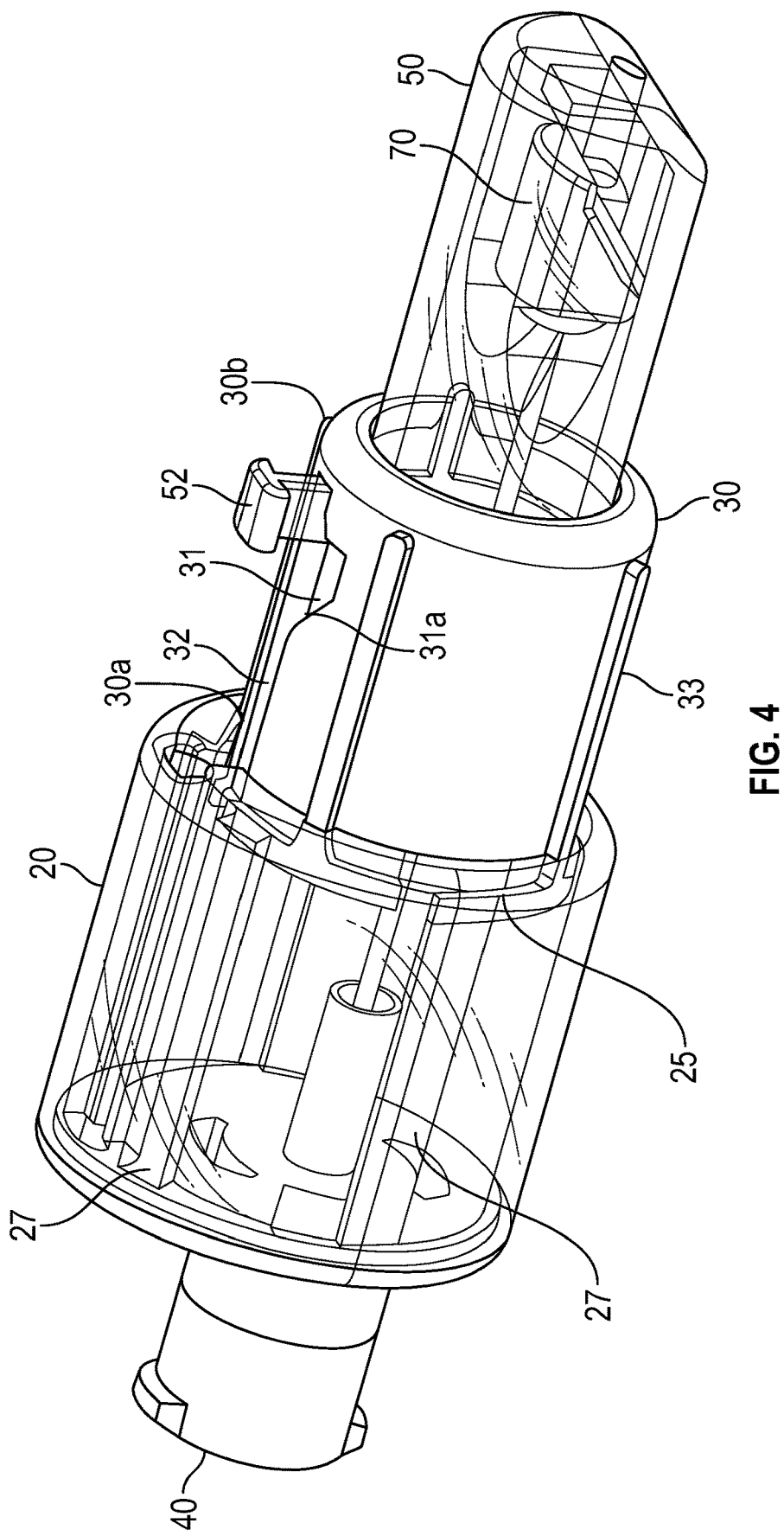
FIG. 4 illustrates a perspective view of a safety needle device shown in FIG. 1 in an extended state.

In one or more embodiments, as shown in FIGS. 1-4, the one or more protrusions 52 of retractable sleeve 50 comprise a protrusion radially extending from a proximal portion of the retractable sleeve. FIGS. 2 and 4 show a first embodiment having at least one protrusion in the shape of a T-Bar (T-shaped protrusion) which keys with an opening 53 the retractable sleeve 50 to housing 20. In the embodiment shown, the opening 24 is complementary in shape to the protrusion 52, and the opening 24 is a T-shaped opening. In an initial state, as shown in FIGS. 1 and 2, tether 30 holds retractable sleeve 50 in an initial position with the needle distal tip 44 exposed. Upon movement of retractable sleeve 50, the T-shaped protrusion causes tether 30 to rotate until the one or more protrusions 52 shifts from a first guide path 31 to a second guide path 32 and the tether 30 is no longer held within housing 20. As insertion of needle cannula 42 continues, one or more protrusion 52 travels proximally along the second guide path. Upon removal of the needle cannula 42 from a patient, the T-shaped protrusion 52 travels distally along the second guide path of tether 30, and tether 30 extends out of the distal end of the housing 20. As shown in FIGS. 1-4, in one or more embodiments, the locking member 70 is in the form of a sliding block to lock out the safety needle device. The needle holds the device in the initial position until it exits both the block and sleeve centering holes. Once the needle is out of both holes, the block is no longer constrained and the spring in the device pushes the block down the ramp misaligning the block and sleeve holes thereby preventing the needle from exiting the device once again. In this way, the device is a single-use passive safety needle device, as the sleeve 50 automatically covers the distal end of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action. The sliding block is discussed in more detail below.

In another embodiment (see FIG. 9), the one or more protrusions 52 comprise a first protrusion radially extending from a proximal portion of the retractable sleeve and having a height H1 and a second protrusion radially extending from a distal portion of the retractable sleeve and having a height H2, the height H1 of the first protrusion being greater than the height H2 of the second protrusion. In yet another embodiment, the one or more protrusions comprise a single radially extending protrusion having a first portion having a first height and a second portion extending laterally from the first portion, the second portion having a second height that is less than the first height. In one or more embodiments, the second protrusion contacts the enlarged first guide path when the retractable sleeve is in the initial position and rotates the tether when the retractable sleeve is moved proximally toward the second position.

As shown in FIGS. 2-4, distal end 22 of housing 20 couples to tether 30 such that the tether 30 is configured to move along and at least partially rotate about a central axis. Distal end 34 of tether 30 couples to a proximal end of retractable sleeve 50. A channel and an aperture are included in the retractable sleeve 50 in order to permit the needle cannula 42 and distal tip 44 of needle cannula 42 to pass therethrough.

The proximal end of retractable sleeve 50 includes a one or more protrusions 52 configured to move between an initial position, a retracted position and an extended position with respect to the housing 20, wherein the initial position partially exposes a distal tip 44 of the needle cannula 42, the retracted position fully exposes the needle cannula 42, and the extended position fully covers the distal tip 44 of the needle cannula 42. The slot of the tether 30 includes a first guide path 31 and a second guide path 32 are disposed on the body of the tether and are configured to direct the retractable sleeve 50 during movement. In one or more embodiments, the first guide path, and second guide path are configured to slidingly receive the one or more protrusions of the retractable sleeve 50.

Retractable sleeve 50 is slidably mounted and movable in the distal opening 24 of the housing body to slidably accommodate and encase needle cannula 42 projecting axially from housing 20.

As illustrated in several of the drawings, most notably FIGS. 1 and 2, retractable sleeve 50 is generally comprised of a tubular portion and is slidably retractable along the length of the needle cannula 42 such that a distal tip 44 of the needle cannula 42 is partially exposed and protruding from the distal end of the retractable sleeve 50 when in an initial position so as to be visible to a user. A substantial or entire portion of needle cannula 42 is exposed when the retractable sleeve 50 is in its retracted position. The length of needle cannula 42 which extends from the hub 40 in a distal direction is completely encased when retractable sleeve 50 is in its extended position, as shown in FIG. 4.

The inside diameter of the retractable sleeve 50 is selected so that it will fit closely over needle cannula 42. The retractable sleeve 50 may be made of any suitable material, but preferably of a polymer which is tough enough to protect needle cannula 42.

In one or more embodiments, movement of the retractable sleeve 50 from the initial position to the retracted position distally moves the one or more protrusions 52 of the retractable sleeve 50 from the enlarged first guide path 31 of the tether, contact a ramping surface 31a and then move to the narrowed second guide path 32 of the tether. In one or more embodiments, the tether 30 rotates with respect to the housing 20 during movement of the retractable sleeve from the initial position to the retracted position. Rotation of the tether 30 from the initial position to the second position guides the one or more protrusions 52 of the retractable sleeve from the enlarged first guide path 31 of the tether to the narrowed second guide path 32 of the tether.

In one or more embodiments, the enlarged first guide path 31 of the tether intersects the narrowed second guide path 32 of the tether. In one or more embodiments, the narrowed second guide path is generally parallel to a central axis and extends along the tether body. In one or more embodiments, the enlarged first guide path may comprise an angle, curvature or taper relative to a central axis. The angle, curvature or taper of the first guide path 31 may allow the one or more protrusions 52 to shift from the first guide path 31 to the second guide path 32.

The proximal end 51 of retractable sleeve 50 includes one or more protrusions 52 that extends radially outward from the proximal end of retractable sleeve 50 and is configured to engage one or more paths formed on the inside surface of the housing body 23. In one or more embodiments, one or more protrusions 52 may be an outwardly extending peg that seats against a ledge of the distal end of the housing as. As shown in FIG. 1, housing 20 has an opening 24 that receives the retractable sleeve 50 and its one or more protrusions 52.

In one or more embodiments, retractable sleeve 50 may be disposed and movable in the housing body 23. The retractable sleeve 50 is spring loaded, and is supplied to the user with the retractable sleeve 50 partially covering the needle cannula 42 so that the distal tip of the needle cannula is exposed and visible in an initial state, as shown in FIG. 1. In the initial state, the one or more protrusions 52 of the retractable sleeve 50 is disposed in the first guide path of the housing body. In one or more embodiments, the one or more protrusions is a peg. Upon administration of the injection, the retractable sleeve 50 moves from an initial position whereby the distal tip 44 of the needle cannula 42 is exposed to a retracted position whereby the needle cannula is increasingly exposed so that the needle cannula may penetrate the injection site. As shown in FIGS. 2 and 4, the tether 30 rotates with respect to the housing 20 during movement from the initial position to the retracted position.

During administration of an injection to a patient, the application of force by the user in the distal direction causes the one or more protrusions 52 of retractable sleeve 50 to move in a proximal direction such that one or more protrusions switches from the first guide path of the housing body to second guide path of the housing body. Rotation of the retractable sleeve 50 from the initial position to the retracted position transfers the one or more protrusions 52 of the retractable sleeve from the first guide path 31 on the slot of the tether to the second guide path 32 on the slot of the tether. In or more embodiments, the retractable sleeve translates from the initial position to the retracted position without impediment.

A continued application of force by the user in the distal direction causes rotational movement of tether 30 causing one or more protrusions 52 to move from the first guide path 31 of the tether to a narrowed second guide path 32.

The movement of the one or more protrusions from the enlarged first guide path inhibits or prevents counter-rotation of the tether 30, which in turn prevents the one or more protrusions 52 from shifting back into the enlarged first guide path 31 at intersection between the first guide path 31 and the second guide path 32. In one or more embodiments, a tether reverse prevention element prevents the tether from moving back to the first position after entering a second position. In one or more embodiments, the tether reverse prevention comprises one-way ratchet arms or a small detent bump. Detent bumps may allow for the device to be purposefully reset after sleeve depression to aid in manufacturability especially when needle lubing is required.

Upon continued application of force by pressing retractable sleeve 50 against the skin of a patient at the location where it is desired to insert needle cannula 42, retractable sleeve 50 retracts into housing 20 allowing the injection site to be penetrated by the needle tip and needle cannula.

Upon completion of an injection to the patient, the user withdraws the needle cannula from the patient, thus causing the stored energy of spring element 90 to allow one or more protrusions 52 of the retractable sleeve 50 to proceed along the narrowed second guide path 32 to allow retractable sleeve 50 to fully cover needle cannula 42 in the extended position. The spring element 90 biases the retractable sleeve 50 in a distal direction to cover the distal tip 44 of needle cannula 42 causing activation of the locking member to prevent further translational movement of the retractable sleeve 50 within the housing body 23. Movement of the retractable sleeve from the retracted position to the extended position engages the locking member 70 to a distal tip 44 of the needle cannula 42. Thus, a single-use passive safety needle device is provided in which the needle distal tip 44 is shielded by a sleeve or sheath automatically after the needle cannula is removed from a subject or patient. A practitioner or user of the device does not have to activate the sleeve or sheath by pressing a button on the device, twisting the device or taking any other action. The sliding block is discussed in more detail below.

In one or more embodiments, the locking member 70 is disposed on the retractable sleeve 50 and rides along the needle cannula 42 until the locking member 70 covers the distal tip 44 of the needle cannula 42 in the extended position. In one or more embodiments, the locking member 70 inhibits reuse of the safety needle device 10 by inhibiting further translational movement of the retractable sleeve 50 within the housing body 23. Needle cannula 42 is obscured from view when the retractable sleeve is in the extended position. As shown in FIG. 4, as the injection is completed and the distal tip 44 of needle cannula 42 is pulled from injection site, the stored force of spring element 90 causes the retractable sleeve 50 to extend, and at the end of the stroke, a second locking member extends over the distal tip 44 of the needle cannula 42 to lock the retractable sleeve 50 thereby completing a passive safety lock-out. In one or more embodiments, the locking member may comprise a clip, latch, a gate, or sliding block to shield the distal tip of the cannula. In one or more embodiments, the locking member may be metal. In one or more alternate embodiments, the locking member may be plastic.

In one or more embodiments, movement of the retractable sleeve from the retracted position to the extended position engages the locking member to a distal tip of the needle cannula.

In one or more embodiments, the locking member inhibits reuse of the passive safety needle device by inhibiting translation of the retractable sleeve.

In one or more embodiments, the locking member may comprise a metal clip, bead and spring plate, tumbling block, and a living hinge built into the sleeve. In one or more embodiments, the locking member may comprise one or more plastic cantilever arms disposed on the retractable sleeve, tether, or housing to lock the device.

Referring now to FIGS. 1 and 2, the safety needle device 10 is illustrated in an initial state wherein the retractable sleeve 50 is in a partially retracted configuration. Further retraction of the retractable sleeve 50 is generally initiated by a user applying pressure on the safety needle device 10 and/or syringe in the distal direction, which thereby encourages the retractable sleeve 50 proximally against the bias of the spring element 90. This retraction of the retractable sleeve 50 in turn further exposes the distal tip 44 of the needle cannula 42 and initiates penetration by the needle cannula 42 into the patient's skin. The one or more protrusions of the retractable sleeve, which is initially positioned in the enlarged first guide path 31, directs the retractable sleeve 50 to immediately move toward the narrowed second guide path 32. As the retractable sleeve 50 moves proximally, the one or more protrusions 52 passes through the narrowed second guide path 32 thereby encouraging the tether 30 to rotate about the axis. Upon reaching the intersection of the enlarged first guide path and the narrowed second guide path, rotation of the tether prevents the one or more protrusions 52 from returning to the enlarged first guide path.

Spring element 90 includes a proximal end, a main body, and a distal end. In one or more embodiments, as shown in FIG. 1, spring element 90 comprises a compression or coil spring. The spring element 90 biases the retractable sleeve from the retracted position to the extended position.

In one or more embodiments, spring element 90 engages and extends between the proximal end of the retractable sleeve and the proximal end of the housing. The spring biases the retractable sleeve 50 toward an initial position in which the one or more protrusions 52 of the retractable sleeve 50 is biased into engagement with the first guide path located at the distal end of the housing body 23 allowing the distal tip 44 of the needle cannula 42 to be exposed and visible in the initial position. The retractable sleeve 50 completely covers the distal tip 44 of the needle cannula 42 in the extended position. Many types of springs may be employed, such as but not limited to a helical coil spring, conical spring, wave-spring, Belleville washer, or the like. In some embodiments, the spring element 90 is configured to facilitate retraction of the retractable sleeve 50 by a user applying distal pressure to the syringe and/or the safety needle device 10 with just one hand.

Safety needle device 10, and components thereof, can be formed using many manufacturing processes sufficient to provide the desired shape of the components. In some embodiments one or more components are made by a molding process, such as but not limited to injection molding, compression molding, blow molding, transfer molding, or similar. In some embodiments, one or more components are formed by forging, machining, casting, stamping, extrusion, a combination thereof, or the like.

In some embodiments, the safety needle device 10 is constructed from a biocompatible material. In some arrangements one or more of the components of the safety needle device 10 are plastic (e.g. polyurethane, etc.) or metal (e.g., stainless steel, etc.). In some embodiments, the housing 14 and/or the retractable sleeve 50 are constructed of materials that are either translucent or opaque.

In some embodiments, movement of the retractable sleeve 50 automatically engages the locking member 70. In some embodiments, movement of the retractable sleeve 50 from an about fully retracted position to an about fully extended position automatically prevents or inhibits reuse of the safety needle device 10.

Retractable sleeve 50 has one or more protrusions 52 are aligned with first guide path 31 of tether 30. The retractable sleeve 50 is slidingly moved through the distal opening 24 of housing 20. The needle cannula 42 is coupled with the needle support 41 of the housing 20. The spring element 90 is inserted into the housing body 23 and positioned to bias the retractable sleeve 50. Upon withdrawal of the needle cannula 42 from the patient, the stored spring energy of the spring element 90 to distally extend the retractable sleeve 50. As the retractable sleeve 50 distally extends, it covers the needle cannula 42 into the channel of the hub body thereby covering the distal end of the needle cannula 42. The distal movement of the retractable sleeve 50 also slides the one or more protrusions 52 along the second guide path.

As shown in FIG. 4, upon reaching the retractable sleeve 50 reaching the distal tip 44 of the needle cannula 42, the locking member 70 moves distally over the distal tip to cover the distal tip 44 of the needle cannula 42 to prevent reuse of the safety needle device 10. The retractable sleeve 50 has been fully extended and fully covers the needle cannula 42. The locking member 70 thus presents a physical stop to inhibit the retractable sleeve 50 from being proximally retracted again.

Therefore, some embodiments of the present disclosure utilize one or more protrusions 52 on the retractable sleeve traveling along a first guide path 31 and second guide path 32 disposed on tether 30. Once injection begins, the one or more protrusions 52 on the retractable sleeve 50 travels along the a first guide path 31 and second guide path 32 rotating the tether from an initial position to a second position as it moves axially. At this point, the user can continue to insert the needle to the desired depth in the patient and the tether 30 will move axially within the second guide path 32 of the tether. Upon removal of the needle cannula, spring element 90 within the system will push the retractable sleeve 50 down the second guide path 32 to a final position and the locking member 70 will automatically cover the distal tip 44 of the needle cannula 42 thereby passively protecting the user from needle stick injury. In this way, a single-use safety needle device is provided that has a sheath or a sleeve that automatically activates when a subject is injected with the device and the needle has been removed from the patient.

In one or more embodiments, the tether includes one or more ribs 33 that interact with one or more guide tracks disposed on the inner surface of the housing body. The one or more ribs 33 on tether 30 interact with one or more guide tracks 27 within the housing 20 to capture the tether 30 within the housing 20 in the initial position. Each rib 33 slidably engages each guide track 27, and upon activation, the each of one or more ribs 33 slidably moves along each shelf 25 within the housing 20 to one or more openings such that the one or more ribs 33 no longer constrain the tether 30 to the housing 20. Once rotation of tether 30 is completed, the one or more ribs disposed on the top surface of the tether 30 snap into the one or more guide tracks disposed on the inner surface of the housing body. The one or more ribs 33 serve to keep tether 30 from rotating back to the initial position ensuring that final lockout with locking member 70 will occur. At this point, the user can continue to insert the needle to the desired depth in the patient and the retractable sleeve 50 will move axially within the narrowed second guide path. Thereafter, upon removal of the device, the tether and its associated ribs can extend out of the housing allowing the needle tip to be shielded. Contemporaneously, upon removal of the needle cannula, spring element 90 within the system will push the retractable sleeve 50 down the narrowed second guide path to a final position and the locking member 70 will automatically cover the distal tip 44 of the needle cannula 42 thereby passively protecting the user from needle stick injury.

In one or more embodiments, in the initial state, the one or more protrusions of the retractable sleeve interact with the slot of the tether, tether holds the device in such that the distal tip of the needle cannula is exposed and the retractable sleeve and tether are keyed to the housing such that it can only move in and out of the device. In one or more embodiments, one or more ribs of the tether interact with the guide tracks of the housing body to hold the device in an initial state such that the distal tip of the needle cannula is exposed and the retractable sleeve and tether are keyed to the housing such that it can only move in and out of the device. In this state, the tether is constrained along the length of the part so that it cannot extend out of the housing. Upon insertion of the device into a patient, vial, or other medium, the activation feature on the sleeve of the device causes the tether to move from an initial position to a second position. In one or more embodiments, this motion can be rotational or linear. In the second position, the tether is no longer contained within the housing and is allowed to extend out of the housing once the device is removed from the patient, vial, or other medium. As the tether extends out of the housing, the retractable sleeve also disengages from the housing and the tip of the needle is shielded.

Figure 5:
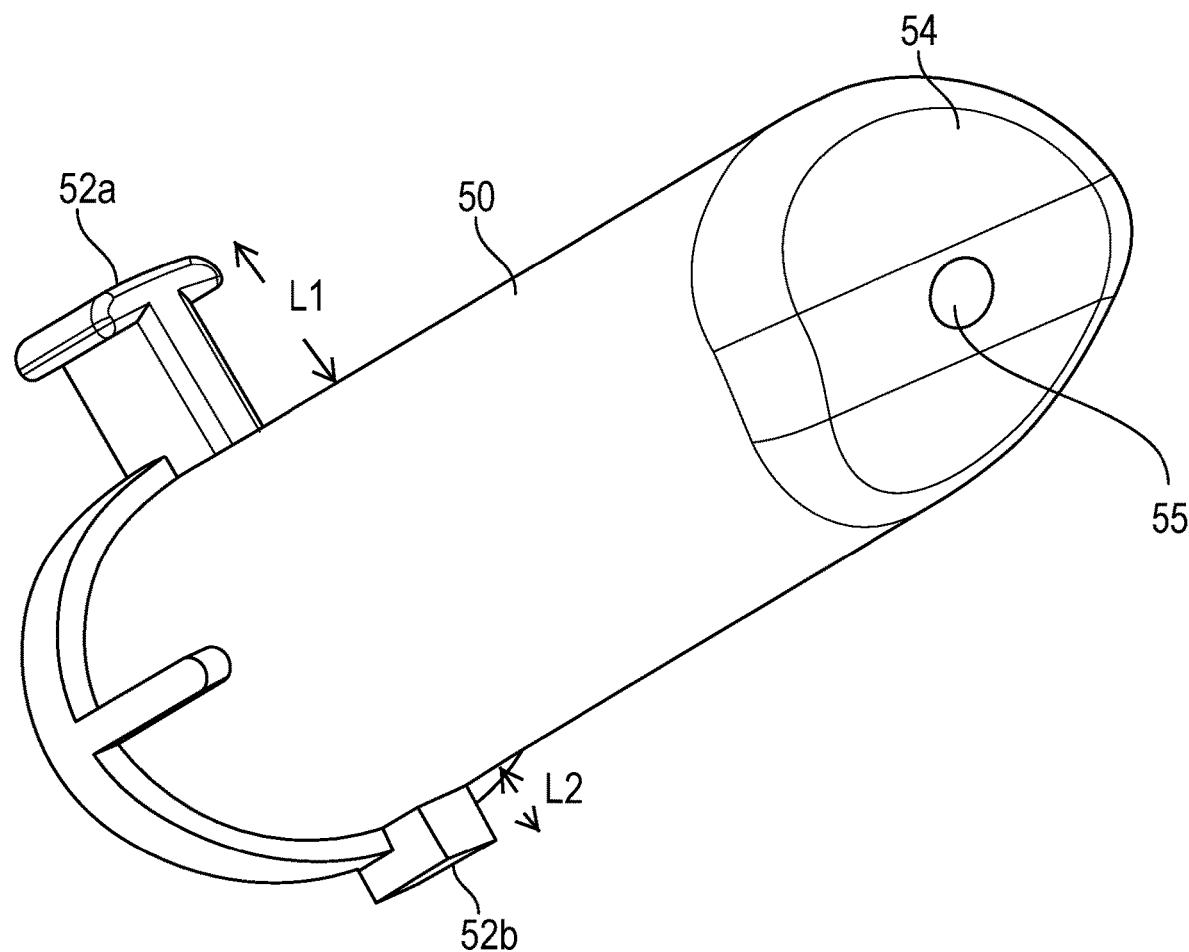
FIG. 5 illustrates a perspective view of a retractable sleeve of a safety needle device according to a first embodiment.
Figure 6:
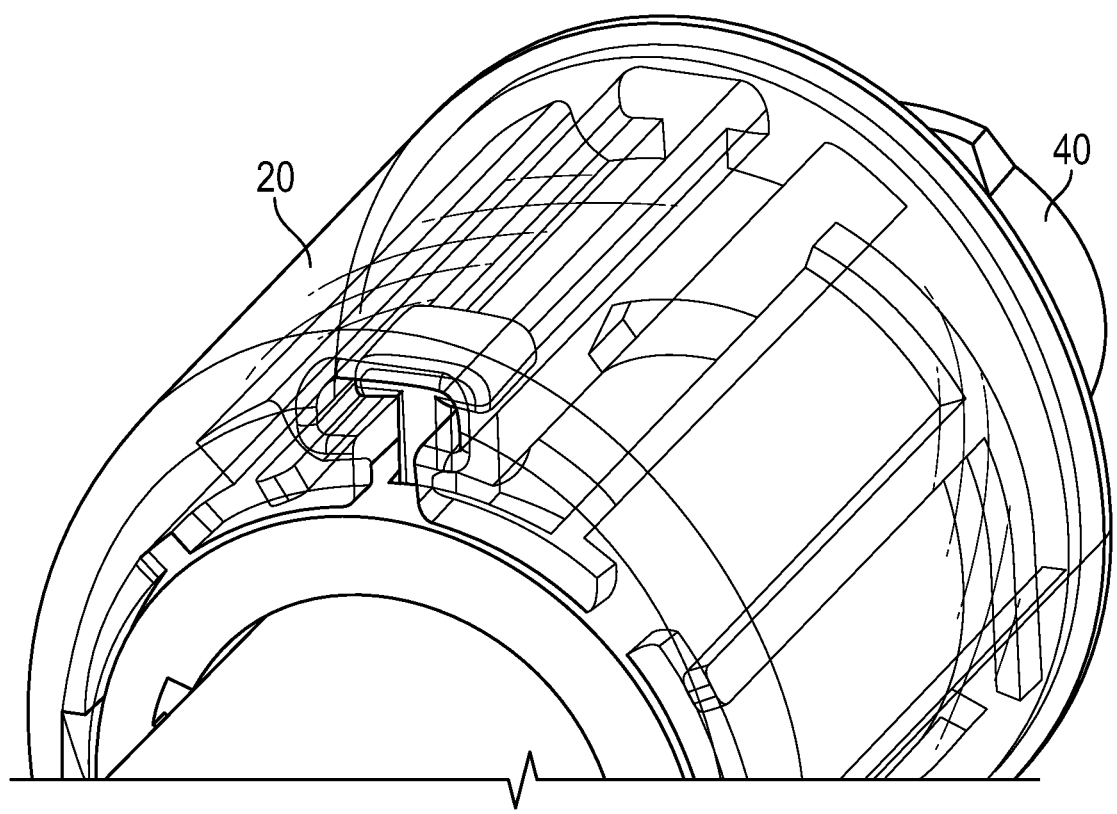
FIG. 6 illustrates a section view of a retractable sleeve keyed to a housing of a safety needle device according to a first embodiment.
Figure 7:
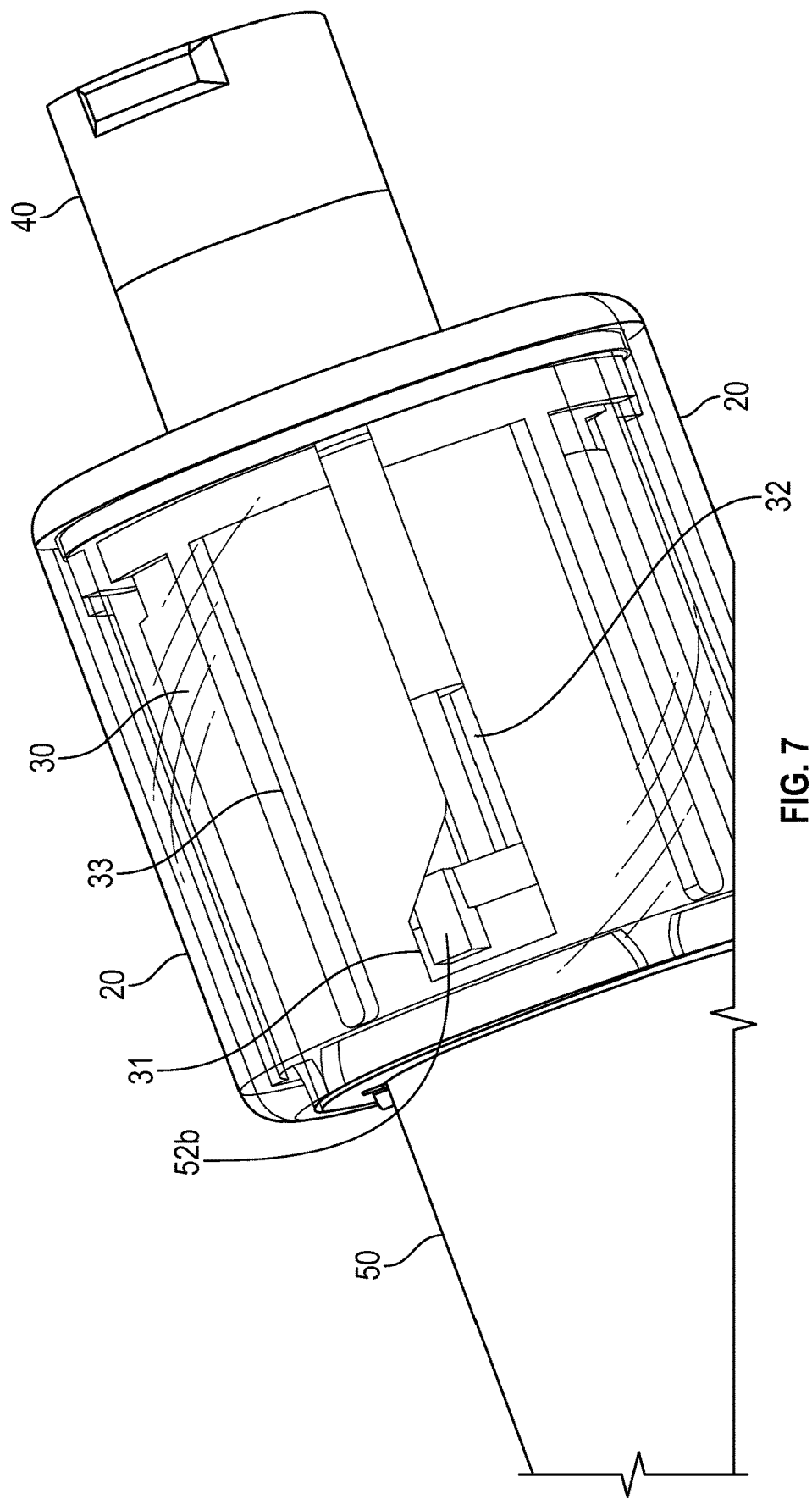
FIG. 7 illustrates a section view of a retractable sleeve keyed to a tether of a safety needle device according to a first embodiment.

In one or more embodiments, the one or more protrusions may comprise a first protrusion 52a of a first length "L1" and a second protrusion 52b having a second length less than "L2". In another embodiment, the first protrusion may be located 90° to the second protrusion. In yet another embodiment, as shown in FIG. 5, the first protrusion 52a may be located 180° to the second protrusion 52b. In one or more embodiments, as shown in FIG. 5, the first protrusion 52a is T-shaped and the second protrusion 52b is in the form of a peg. FIG. 6 shows the embodiment of FIG. 5 in which the first protrusion keys to housing 20 but has no impact on rotating tether 30 to activate the device 10. FIG. 7 shows the embodiment of FIG. 5, in which the second protrusion 52b engages with the tether 30 and activates the device by causing the tether 30 to rotate. In the shown embodiment, the second protrusion 52b does not engage with housing 20.

Figure 8:
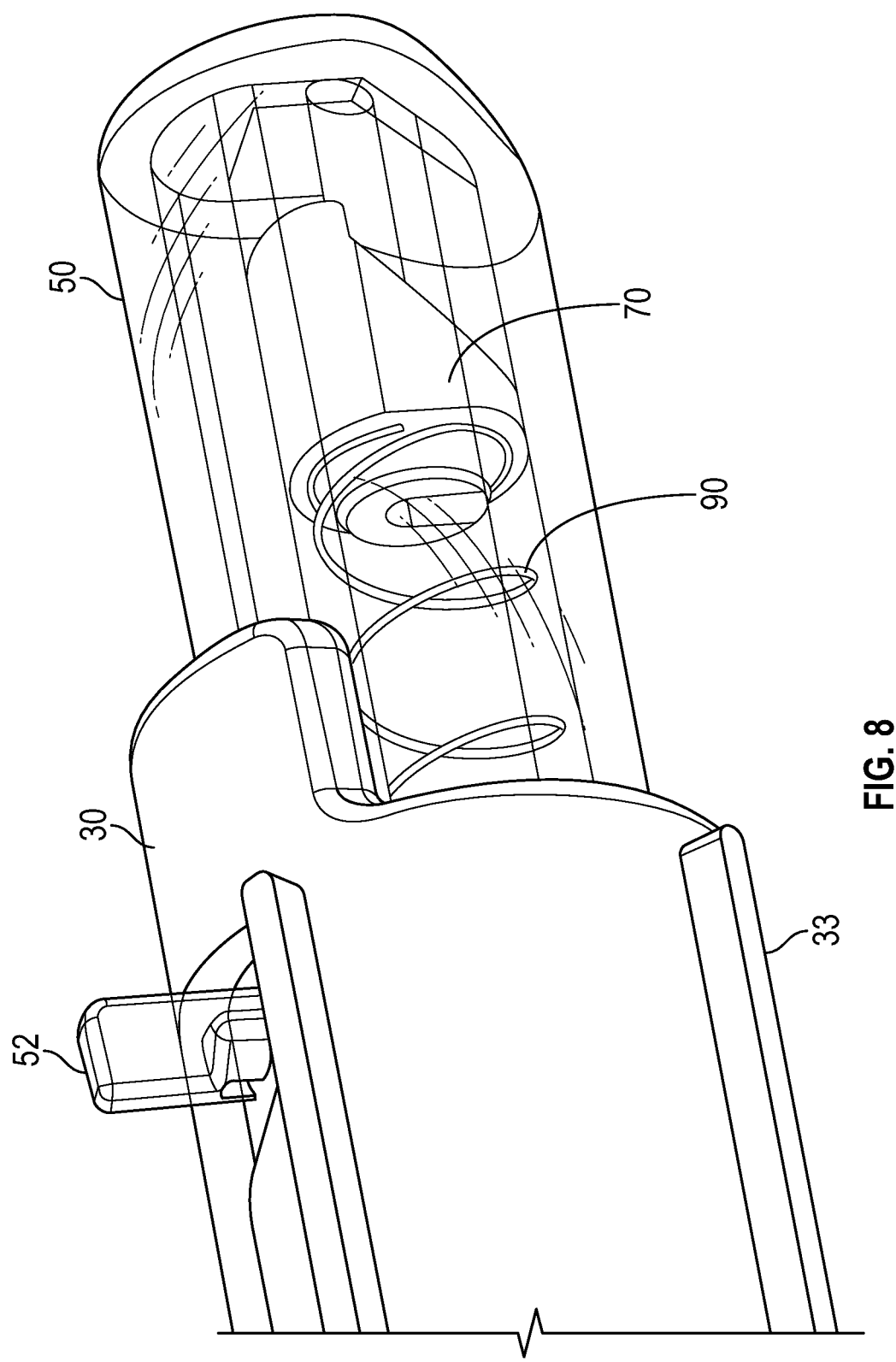
FIG. 8 illustrates a section view of a retractable sleeve keyed to a tether of a safety needle device according to an alternate embodiment having two protrusions.

FIG. 8 shows an alternate embodiment of the retractable sleeve having one or more protrusions in which the first protrusion is in the shape of a T-Bar and the second protrusion is an activation bump. First protrusion interacts with a slot in the housing 20 to rotationally key the housing and the retractable sleeve. The second protrusion is connected to the first protrusion and engages with tether 30 and activates the safety needle device 10 by causing the tether to rotate. The second protrusion does not engage with the housing.

Figure 9:
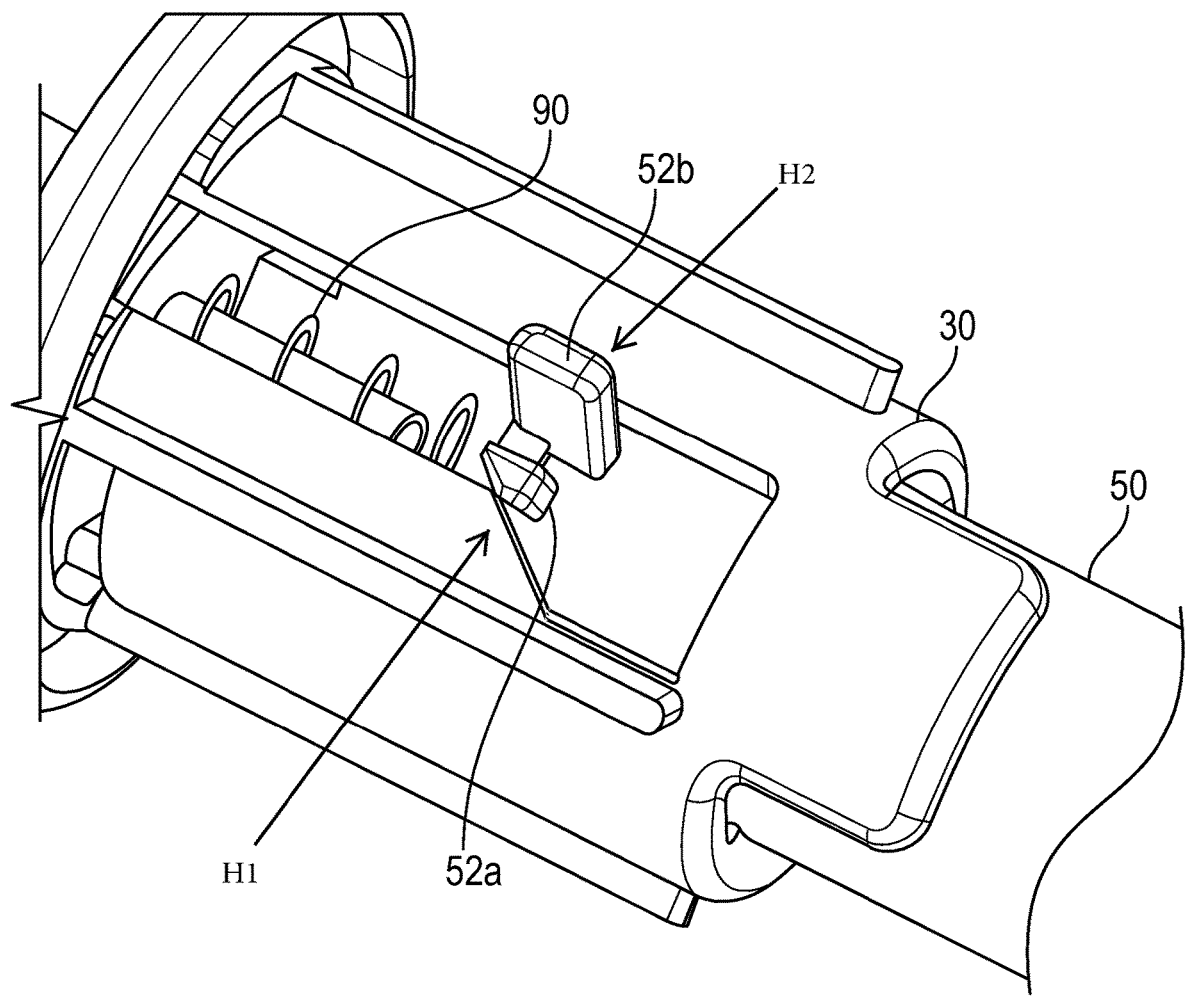
FIG. 9 illustrates a section view of a retractable sleeve keyed to a tether of a safety needle device according to an alternate embodiment having two protrusions.

FIG. 9 shows an alternate embodiment of the retractable sleeve having one or more protrusions in which the first protrusion 52a having a height H1 interacts with a slot in the housing to rotationally key the housing and the retractable sleeve. In one or more embodiments, as shown in FIG. 9, the first protrusion 52a may be adjacent to the second protrusion 52b having a height H2 greater than H1. In one or more embodiments, the second protrusion 52b, in the form of a peg, engages with tether 30 and activates the safety needle device 10 by causing tether 30 to rotate. The second protrusion 52b, in the form of a peg, does not engage with the housing 20.

Figure 10:
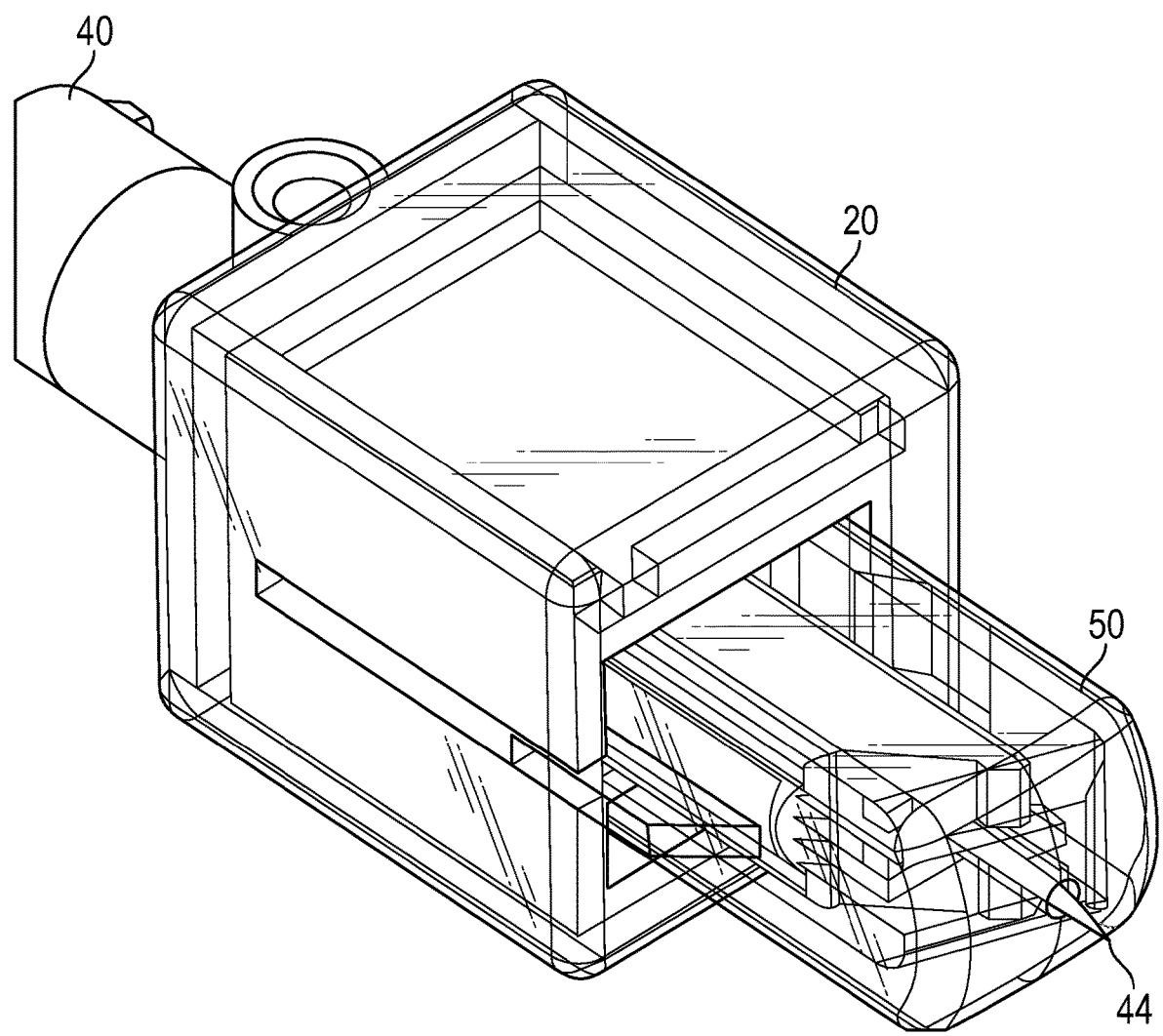
FIGS. 10 and 11 illustrate a perspective view of a retractable sleeve of a safety needle device according to an alternate embodiment utilizing linear motion.
Figure 11:
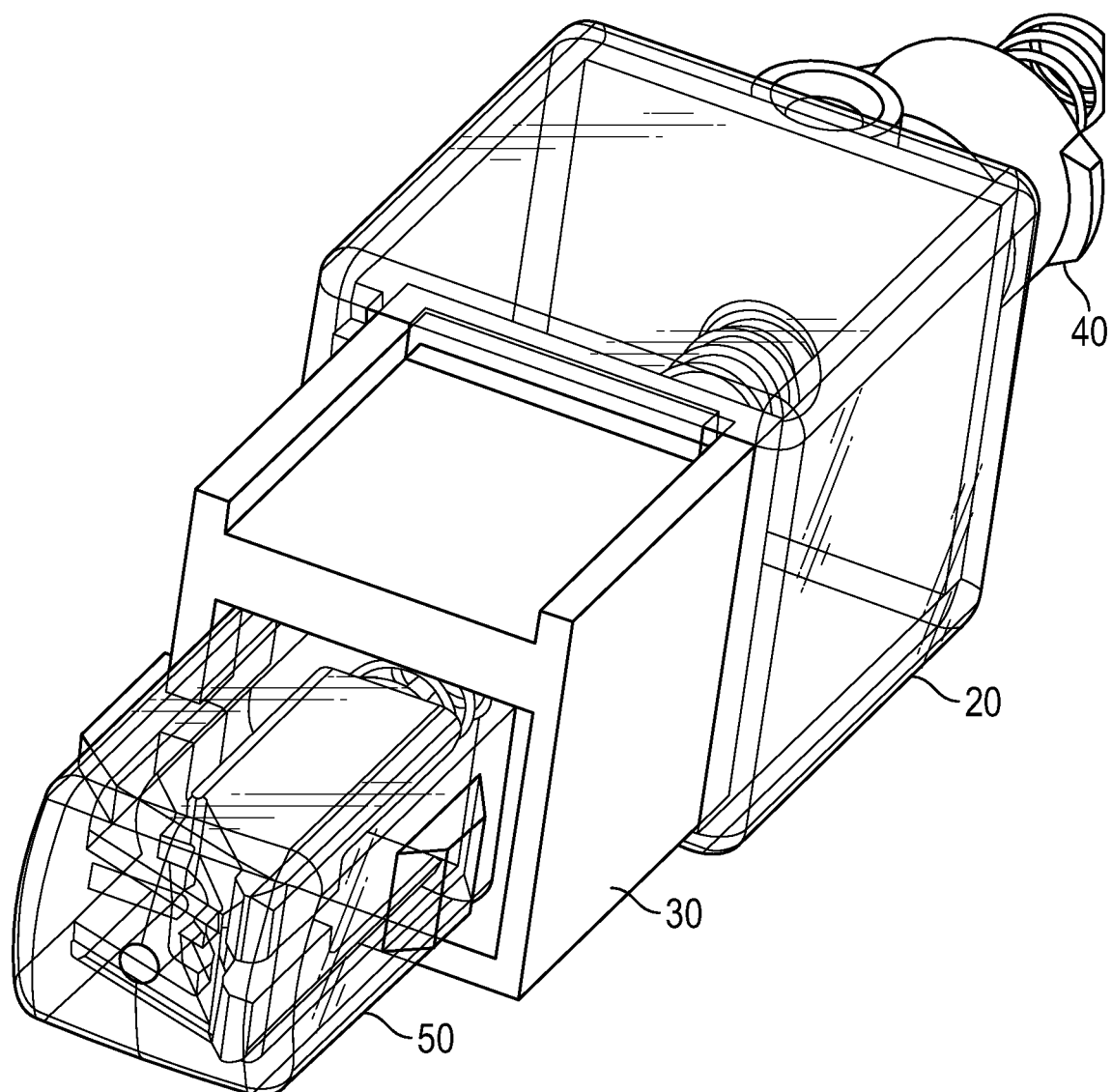

FIGS. 10 and 11 show an alternate embodiment in which tether 30 utilizes linear motion instead of rotational motion. As shown in FIG. 10, retractable sleeve and tether start in an initial position with the needle distal tip 44 exposed and tether 30 retained in housing 20. Upon movement of the retractable sleeve 50 in a proximal direction, one or more bevels on the retractable sleeve 50 interact with tether 30 to move the tether from a starting position to a second position where it is no longer locked to the housing 20. After completion of the injection and upon removal the safety needle device 10 from the patient, retractable sleeve 50 and tether 30 are allowed to fully extend as they are no longer locked to housing 20. As shown in FIGS. 10 and 11, the locking element may be in the form of a sliding block to lock out the safety needle device to prevent re-use and accidental needle stick injury. It is also contemplated that the locking element may be in the form of a metal clip, latch or gate. Thus, a single-use passive safety needle device is provided. The sleeve 50 automatically covers the distal end of the needle after a patient has been injected. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action. The sliding block is discussed in more detail below.

As shown in FIGS. 12-19, in one or more embodiments, the proximal end 51 of retractable sleeve 50 includes a retention hook 54 that extends radially outward from the proximal end of retractable sleeve 50 and is configured to engage the activation latch 80 of the housing body 23.

Figure 12:
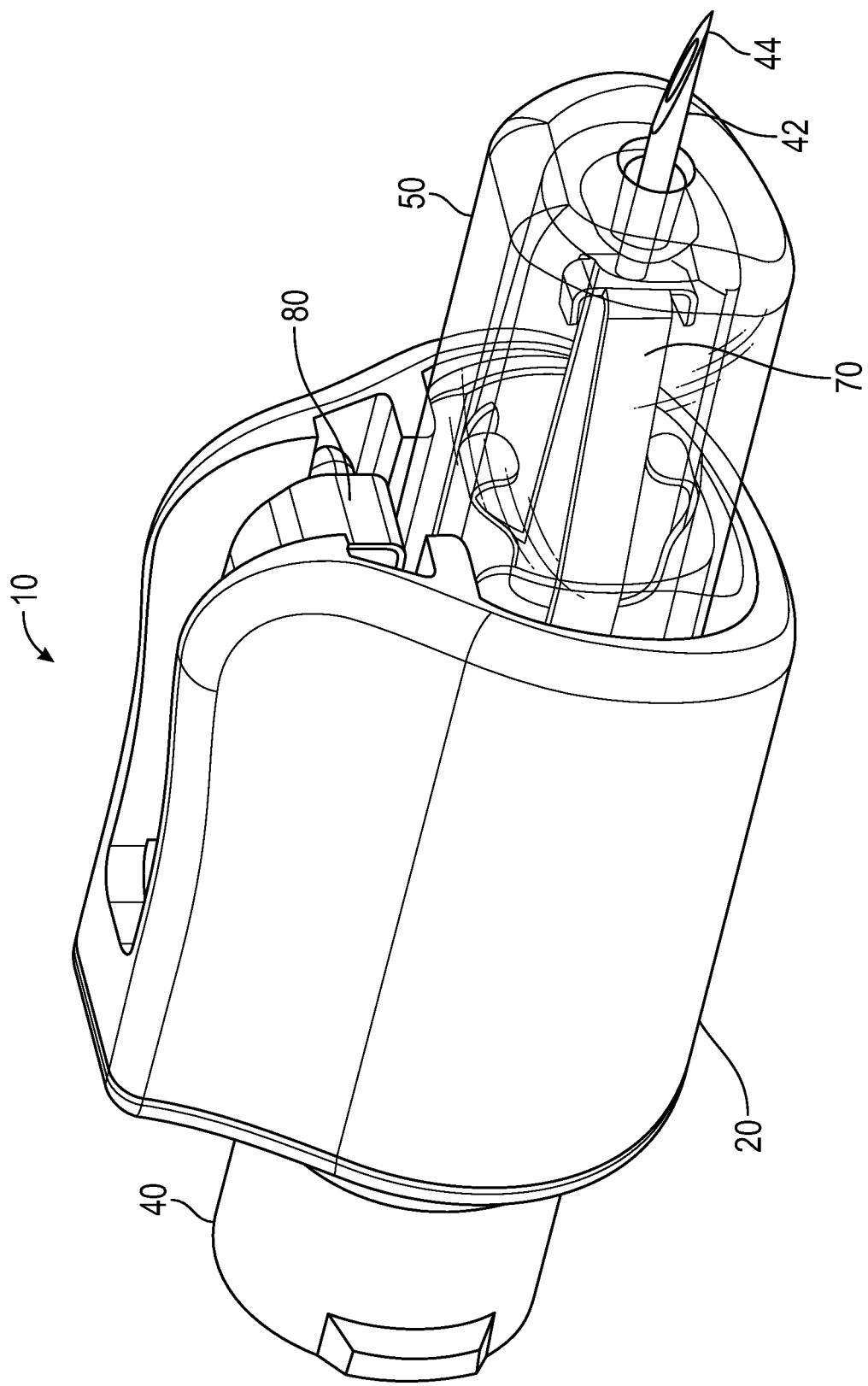
FIG. 12 illustrates a perspective view of a safety needle device according to an alternate embodiment including a retention hook.
Figure 13:
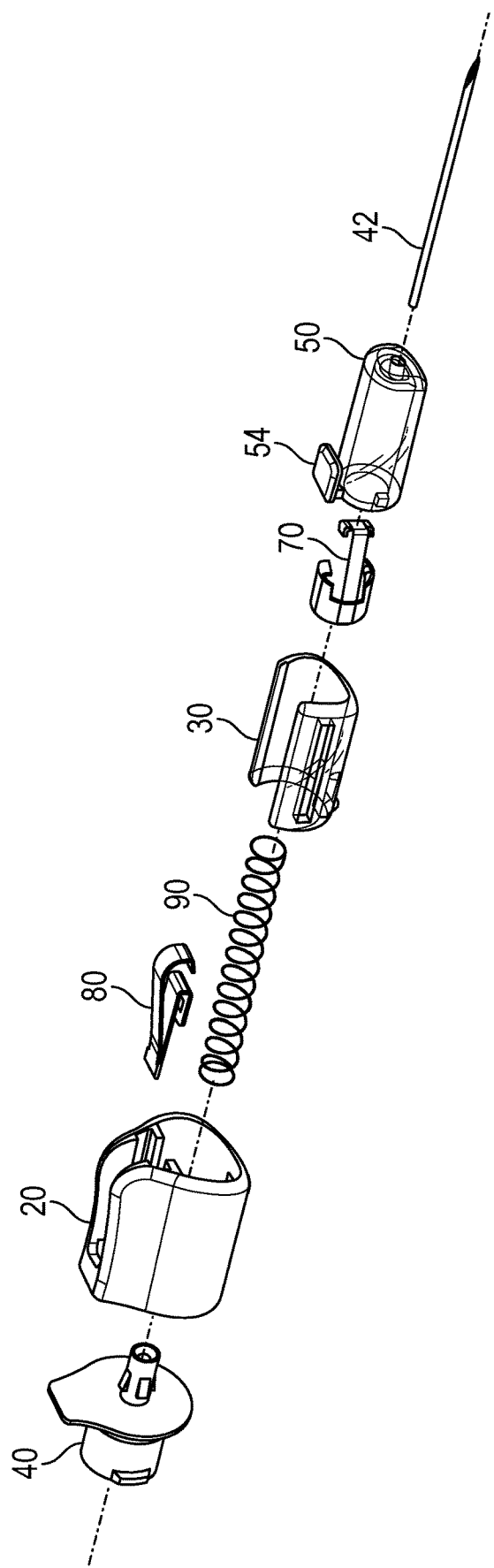
FIG. 13 illustrates an exploded view of a safety needle device of FIG. 12.

FIG. 12 illustrates a perspective view of a safety needle device according to an alternate embodiment including a retention hook 54 and FIG. 13 illustrates an exploded view of a safety needle device of FIG. 12.

As shown in FIG. 12, housing 20 has an opening 24 that receives the retractable sleeve 50. In one or more embodiments, retractable sleeve 50 may be disposed and movable in the housing body 23. The retractable sleeve 50 is spring loaded, and is supplied to the practitioner with the retractable sleeve 50 partially covering the needle cannula 42 so that the distal tip of the needle cannula is exposed and visible in an initial state. Upon administration of the injection, the retractable sleeve 50 moves from an initial position whereby the distal tip 44 of the needle cannula 42 is exposed to a retracted position whereby the needle cannula is increasingly exposed so that the needle cannula may penetrate the injection site.

As shown in FIGS. 12 and 13, one or more embodiments of the safety needle device 10 include an activation latch 80 in combination with a spring element 90. In the initial state both the activation latch 80 and the spring element 90 hold stored energy. Upon beginning injection, the energy in the activation latch 80 is released once the retention hook 54 on the proximal end of the retractable sleeve 50 is released from engagement with the activation latch 80 upon a practitioner depressing the activation latch over a very short distance.

Once the activation latch 80 is released from the retention hook 54 on the proximal end of the retractable sleeve 50, the practitioner can continue to inject the cannula to their desired depth in a patient or vial by either utilizing the full length of the needle or a significantly shorter distance of the needle cannula. Upon removing the needle cannula 42 from a patient, the retractable sleeve 50 automatically advances forward and the stored energy in the spring element 90 is released allowing retractable sleeve 50 to continues to be pushed forward until the a locking member 70 in the form of a lockout latch is able to clip over the distal tip 44 of the needle cannula 42 thereby passively locking out the safety needle device 10 and preventing needle stick injury to the practitioner. In one or more embodiments, activation latch 80 may be a flexible material latch, for example, a metal latch. In one or more embodiments, the locking member 70 in the form of a lockout latch may be a metal latch.

During administration of an injection to a patient, the application of force on the needle device by the practitioner in the distal direction and/or depression of the activation latch 80 by the practitioner cause the retractable sleeve 50 to move in a proximal direction. In or more embodiments, the retractable sleeve translates from the initial position to the retracted position without impediment. A continued application of force by the practitioner in the distal direction causes activation latch 80 to disengage from the retention hook 54 thus activating the locking member 70 in the form of a lockout latch. In one or more embodiments, the locking member 70 in the form of the lockout latch includes a metal latch on a distal end of the retractable sleeve. Movement of the retractable sleeve from the initial position to the retracted position disengages the activation latch 80 from the retention hook 54. In some embodiments, the activation latch 80 is generally resilient, so that the radially inwardly disposed second ends can flex and then return to the original position even after the ends have been radially outwardly deflected. In one or more embodiments, the activation latch 80 may include a latching member, such as a hook, clasp, detent, ratchet, or other structure.

Upon completion of an injection to the patient, the practitioner withdraws the needle cannula from the patient, thus causing the stored energy of spring element 90 to allow the retractable sleeve 50 to proceed to fully covers needle cannula 42 in the extended position. The spring element 90 biases the retractable sleeve 50 in a distal direction to cover the distal tip 44 of needle cannula 42 causing activation of the locking member 70 in the form of a lockout latch to prevent further translational movement of the retractable sleeve 50 within the housing body 23. Movement of the retractable sleeve from the retracted position to the extended position engages the locking member in the form of the lockout latch to a distal tip of the needle cannula.

In one or more embodiments, the locking member 70 in the form of the lockout latch is disposed on the retractable sleeve and rides along the needle cannula until the lockout latch covers the distal tip 44 of the needle cannula 42 in the extended position. In one or more embodiments, the retractable sleeve 50 extends in length beyond the lockout latch. In one or more embodiments, lockout latch comprises a protective clip which can have a V-shape at the distal end to cover the distal tip 44 of the needle cannula 42 in the extended position. In one or more embodiments, the lockout latch inhibits reuse of the safety needle device 10 by inhibiting further translational movement of the retractable sleeve 50 within the housing body 23 by covering the distal tip 44 of the needle cannula 42 in the extended position. Needle cannula 42 is obscured from view when the retractable sleeve is in the extended position. As the injection is completed and the distal tip 44 of needle cannula 42 is pulled from injection site, the stored force of spring element 90 causes the retracting sleeve 50 to extend, and at the end of the stroke, a lockout latch extends over the distal tip of the needle cannula 42 to lock the retractable sleeve 50 thereby completing a passive safety lock-out. In one embodiment, the lockout latch is a metal clip. In this way, the device is a single-use passive safety needle device, as the sleeve 50 automatically covers the distal tip 44 of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action.

Figure 14:
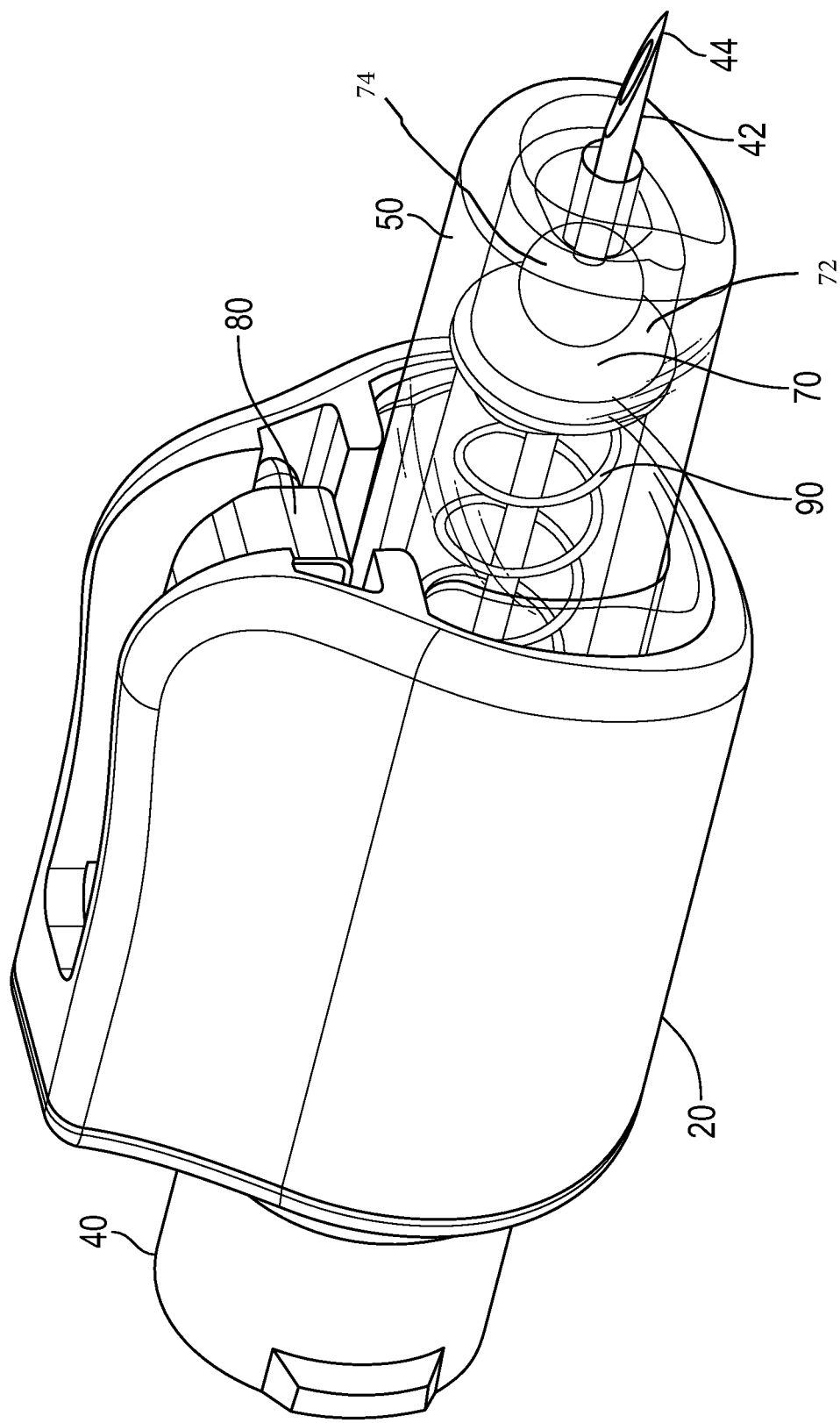
FIG. 14 illustrates a perspective view of a safety needle device according to an alternate embodiment having a locking element with a bead and spring plate.
Figure 15:
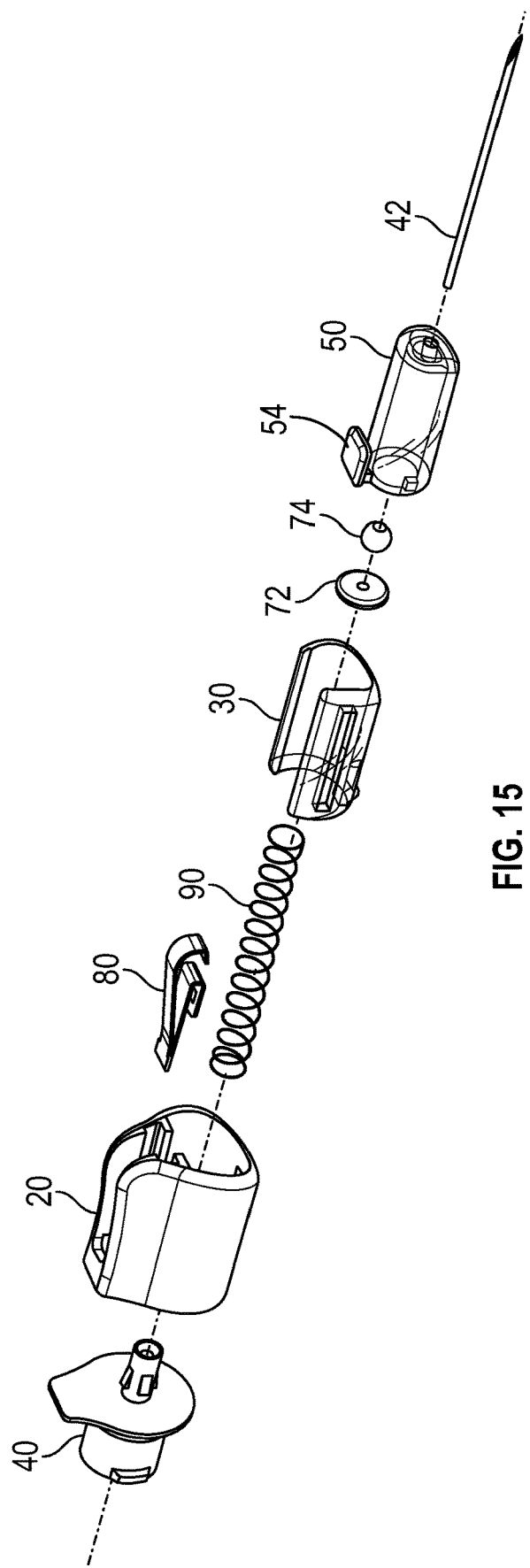
FIG. 15 illustrates an exploded view of a safety needle device of FIG. 14.

FIG. 14 shows an alternate embodiment having a locking member including a bead and spring plate. FIG. 15 shows an exploded view of the embodiment shown in FIG. 14. As shown in FIGS. 14 and 15, locking member 70 may be in the form of a spring plate 72 and bead 74 in combination with a spring element 90 to pivot that bead 74 and spring plate 72 in order to achieve lockout and thereby preventing the needle from re-finding the hole. In one or more embodiment, spring plate 72 and bead 74 are housed inside the retractable sleeve 50 as shown in FIGS. 14-15. Retractable sleeve 50 utilizes the energy in spring element 90 to bias the retractable sleeve upon lockout so that the needle and corresponding holes in the spring plate 72 and bead 74 are no longer co-axial preventing the needle from once again finding the hole.

In one or more embodiments, as shown in FIGS. 14 and 15, spring plate 72 and bead 74, respectively, have a channel within the body of spring plate 72 and bead 74. In an initial state, the cannula is threaded through the channel of both the spring plate 72 and bead 74 allowing the distal tip of the cannula to protrude from the distal end of the retractable sleeve 50 such that distal tip of the cannula is visible to the practitioner. Upon administration of an injection to a patient, the retractable sleeve 50 moves in a proximal direction such that the needle cannula moves out of the channel of both spring plate 72 and bead 74 allowing both spring plate 72 and bead 74 to rotate such that the distal tip 44 of needle cannula 42 is prevented from re-entering the channel within the body of the spring plate 72 and bead 74 to prevent exposure of the practitioner from the distal tip 44 of needle cannula 42.

If the distal tip of the cannula attempts to pass back through the channel of spring plate 72 and bead 74, the distal tip will be buttressed by the body of one or both of the spring plate 72 and bead 74 thus causing the distal tip to remain safely disposed within the housing 20.

Spring plate 72 and bead 74 may be made of strong material to prevent the distal tip 44 of the needle cannula 42 from piercing through the spring plate and bead.

Figure 16:
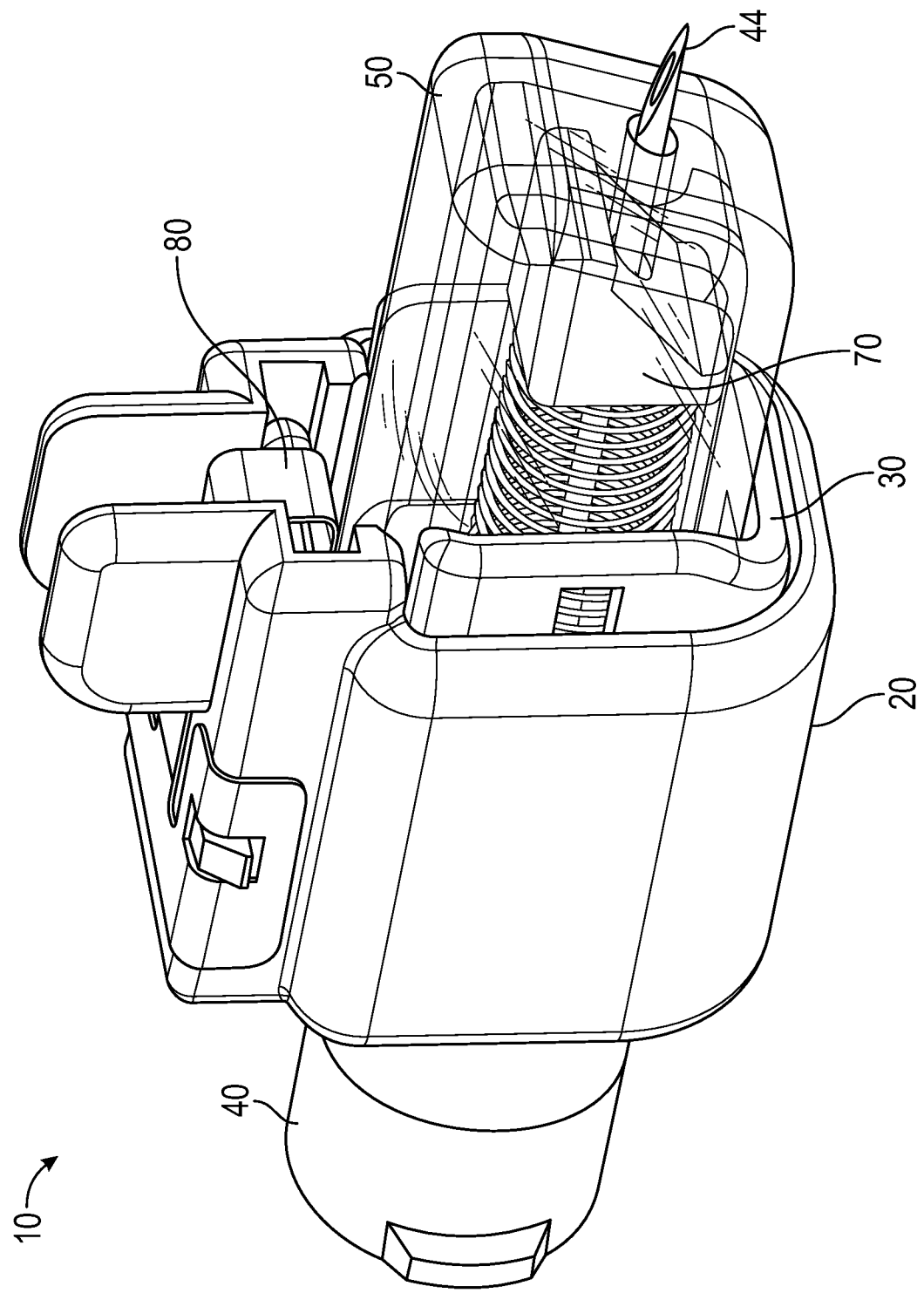
FIG. 16 illustrates a perspective view of a safety needle device according to an alternate embodiment having a locking element in the form of a sliding block.
Figure 17:
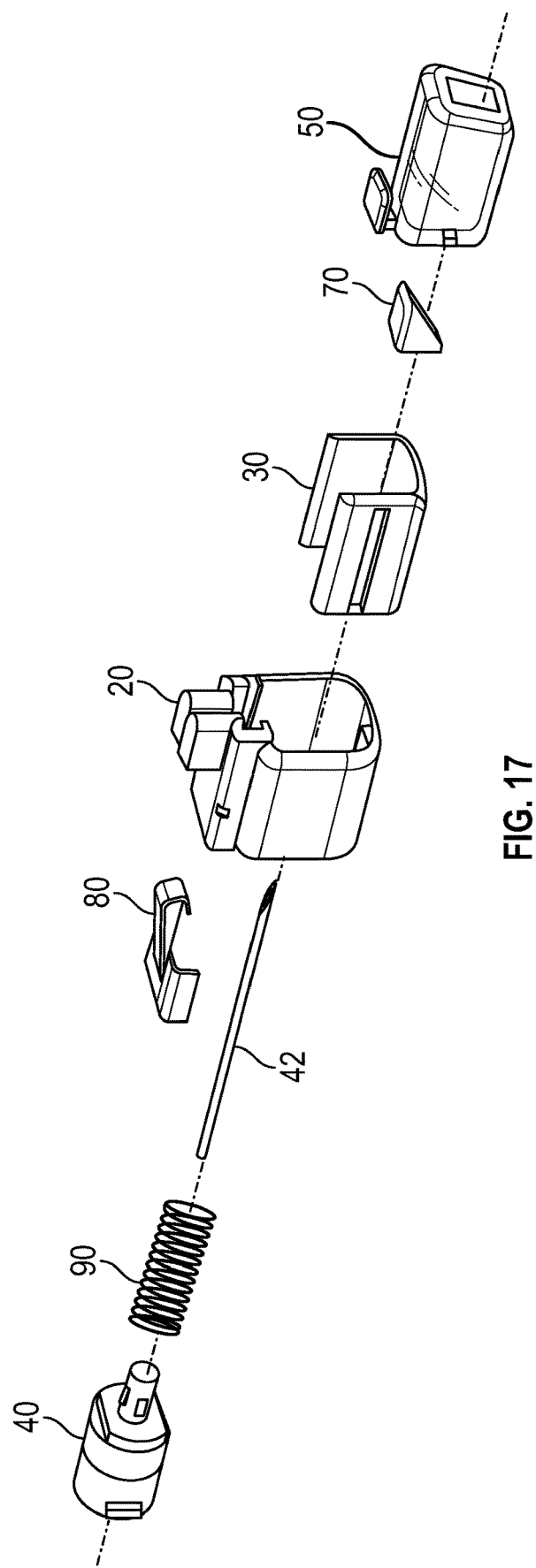
FIG. 17 illustrates an exploded view of a safety needle device of FIG. 16.

FIGS. 16-18 show an alternate embodiment in which locking member 70 is in the form of a sliding block. FIG. 17 shows an exploded view of embodiment shown in FIG. 16. As shown in FIGS. 16-18, locking member 70 may be in the form of a sliding block in combination with a spring element to pivot that sliding block in order to achieve lockout and thereby preventing the needle from re-finding the hole. In one or more embodiment, sliding block is housed inside the retractable sleeve 50 as shown in FIGS. 16-18. As shown in FIG. 18, retractable sleeve 50 utilizes the energy in spring element 90 to bias the retractable sleeve upon lockout so that the needle and the hole are no longer co-axial preventing it from once again finding the hole. In one or more embodiments, sliding block may be configured as an angled plastic component.

In one or more embodiments, as shown in FIGS. 17 and 18, sliding block comprises a block having a channel within the body of the sliding block attached to spring element is provided. In an initial state, the cannula is threaded through the channel such allowing the distal tip of the cannula to protrude from the distal end of the retractable sleeve 50 such that distal tip of the cannula is visible to the practitioner while the spring element exerts force on sliding block to maintain the blocking element in a biased state at the distal end of the retractable sleeve 50. Upon administration of an injection to a patient, the retractable sleeve 50 moves in a proximal direction such that the needle cannula moves out of the channel allowing the sliding block to rotate to an unbiased state such that the cannula is prevented the distal tip 44 of needle cannula 42 from re-entering the diagonal channel within the body of the sliding block to prevent exposure of the practitioner from the distal tip 44 of needle cannula 42.

If the distal tip of the cannula attempts to pass back through the channel, the distal tip will be buttressed by the body of the sliding block thus causing the distal tip to remain safely disposed within the housing 20 and prevented by the tether 30 and sliding block from exiting the confines of the housing 20.

When the needle cannula 42 is withdrawn from the patient, the patient's skin no longer obstructs forward movement of the retractable sleeve 50, and the retractable sleeve 50 then moves to the extended position as shown in FIG. 18. As shown in FIG. 18, the retractable sleeve 50 has an aperture through which the needle cannula 42 extends in an initial position.

The misalignment of the needle cannula 42 with the channel of the sliding block prevents the needle cannula 42 from extending back out of the channel of the sliding block after use. Furthermore, the sliding block may be made of strong material to prevent the distal tip 44 of the needle cannula 42 from piercing through the blocking element. In this way, the device is a single-use passive safety needle device, as the sleeve 50 automatically covers the distal end of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action.

Figure 19B:
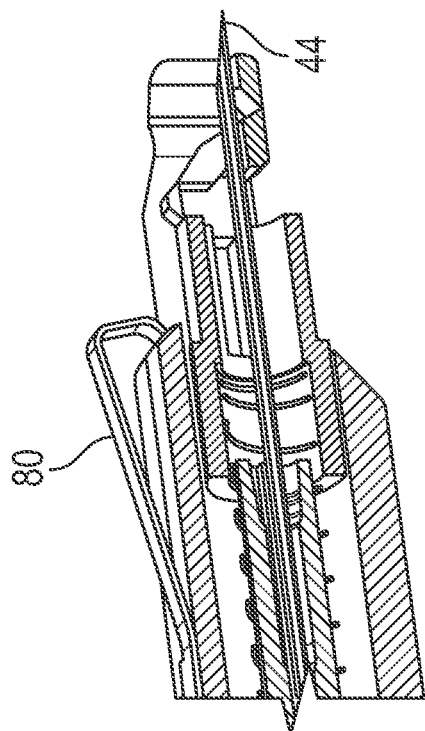
FIG. 19B illustrates a cross-sectional view of the device of FIG. 19A with the sleeve in a partially extended position.
Figure 19C:
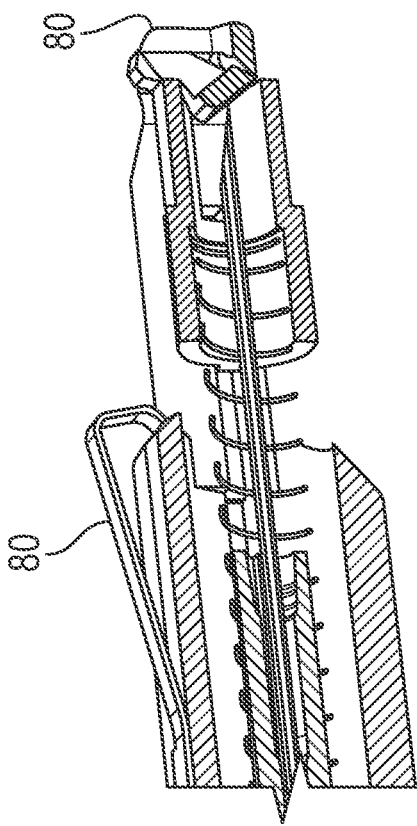
FIG. 19C illustrates a cross-sectional view of the device of FIG. 19A with the sleeve in a retracted position.
Figure 19A:
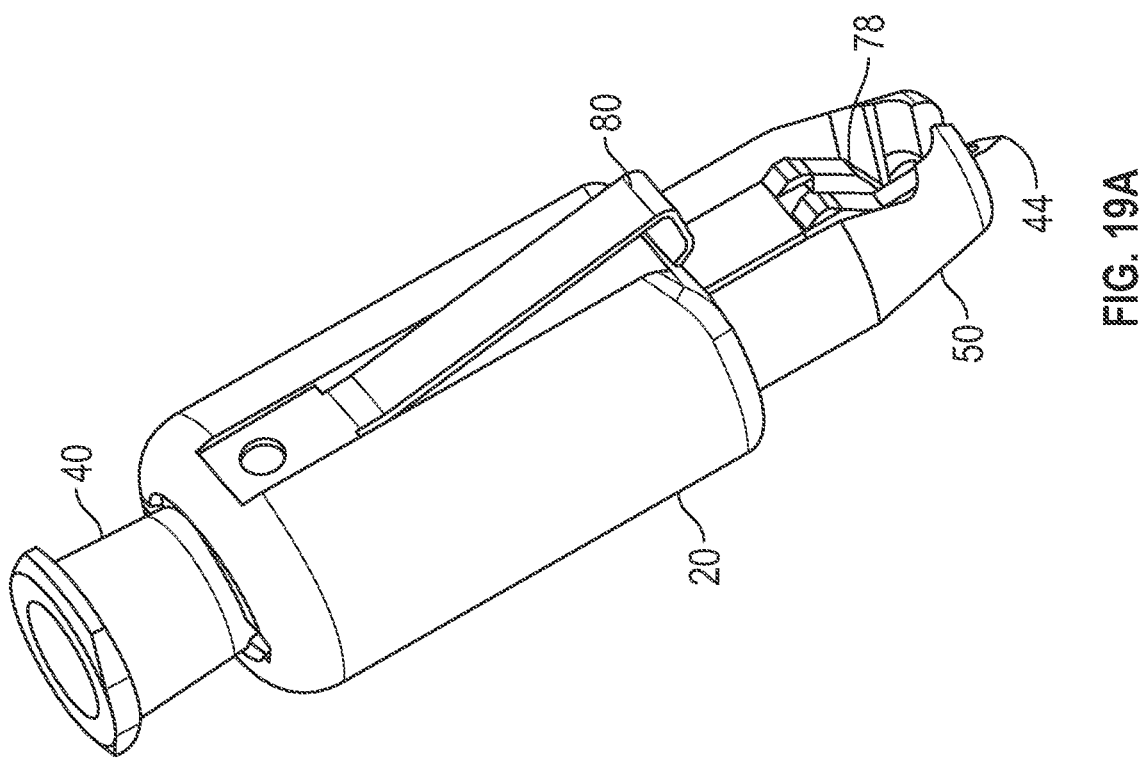
FIG. 19A illustrates a perspective view of a safety needle device according to an alternate embodiment having a living hinge with the sleeve in starting position and locked position.

FIG. 19 shows an alternate embodiment having a locking member including a living hinge 78 in combination with a spring element 90 to bias the living hinge in order to achieve lockout and thereby preventing the needle from exiting the retractable sleeve 50 after completion of an injection. Upon lockout, the distal tip 44 of needle cannula 42 will be buttressed by the body of living hinge thus causing the distal tip to remain safely disposed within the housing 20.

Figure 20C:
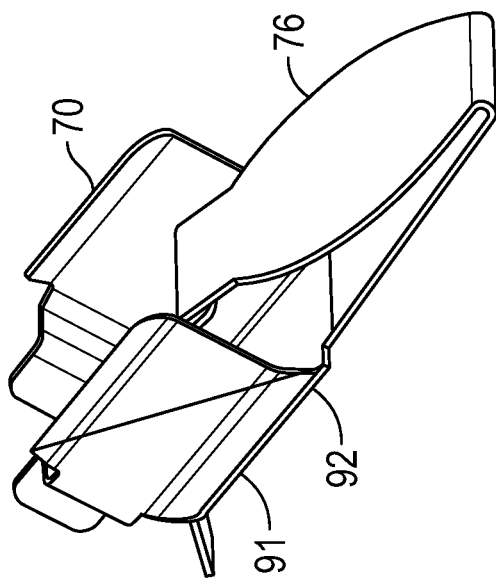
FIG. 20C illustrates a perspective view the latch locking member of the safety needle device of FIG. 20A.
Figure 20B:
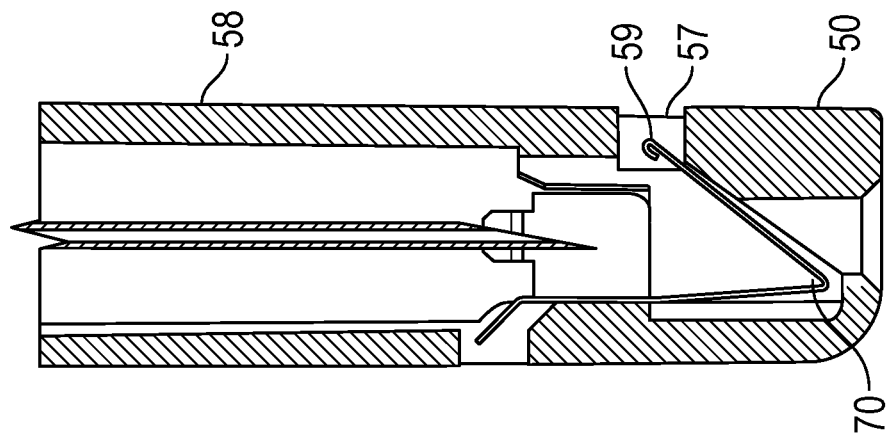
FIG. 20B illustrates a perspective view of a safety needle device of FIG. 20A with the sleeve in an extended position.
Figure 20A:
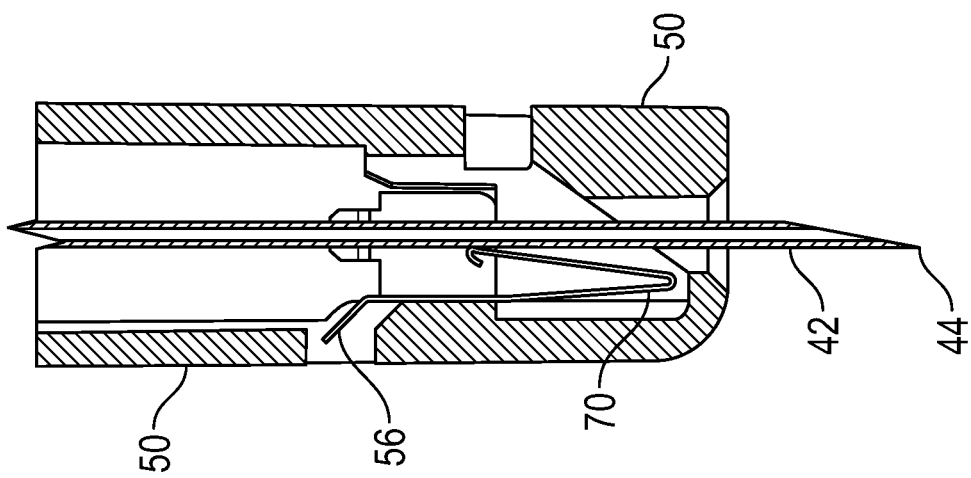
FIG. 20A illustrates a perspective view of a safety needle device according to an alternate embodiment having a tether and latch locking member with the sleeve in an initial position.

FIG. 20 shows yet another alternate embodiment having a locking member 70 in the form of a lockout latch to prevent the needle from exiting the retractable sleeve 50 after completion of an injection. The locking member 70 in the form of a lockout latch has an overall three-dimensional U-shape, including a proximal end 91 and a distal end 92. The proximal end 91 of the locking member 70 is connected to a sidewall 56 of the retractable sleeve. The distal end of the locking member 70 includes a V-shaped biasing member 76 that rests against the needle cannula 42 in an initial state and interacts with a recess 57 on the opposite sidewall 58 of the retractable sleeve 50 when the retractable sleeve is in an extended position. In the starting position, locking member 70 in the form of a lockout latch is disposed in the retractable sleeve and rests in a compressed position against the body of the needle cannula 42. The V-shaped biasing member slides along the needle cannula 42 while the needle cannula 42 is inserted into a subject or a patient, and the sheath or sleeve 50 moves in a proximal direction as the sheath or sleeve 50 end face contacts the patient's or subject's skin. When the needle cannula 42 is removed from the subject or patient, and the sheath or sleeve 50 moves in a distal direction, and the V-shaped biasing member slides past the needle cannula 42 the locking member 70 in the form of a lockout latch covers the distal tip 44 of the needle cannula 42 in the extended position. After the device is activated, a spring element (not shown) pushes the retractable sleeve forward to allow the retractable sleeve 50 to extend past the distal tip 44 of needle cannula 42 which allows stored energy in the compressed V-shaped biasing member 76 to be released such that it activates and locks the device when hook 59 on the distal tip of the V-shaped biasing member 76 interacts with a recess 57 on the opposite sidewall 58 of the retractable sleeve 50. Locking member 70 in the form of a lockout latch is able to clip over the distal tip 44 of the needle cannula 42 thereby passively locking out the safety needle device 10 and preventing needle stick injury to the practitioner. The locking member 70 inhibits reuse of the safety needle device 10 by inhibiting further translational movement of the retractable sleeve 50 within the housing body 23 by covering the distal tip 44 of the needle cannula 42 in the extended position. Needle cannula 42 is obscured from view when the retractable sleeve is in the extended position. In one or more embodiments, locking member 70 in the form of a lockout latch may be a metal latch. In this way, the device is a single-use passive safety needle device, as the sleeve 50 automatically covers the distal end of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action.

Figure 21D:
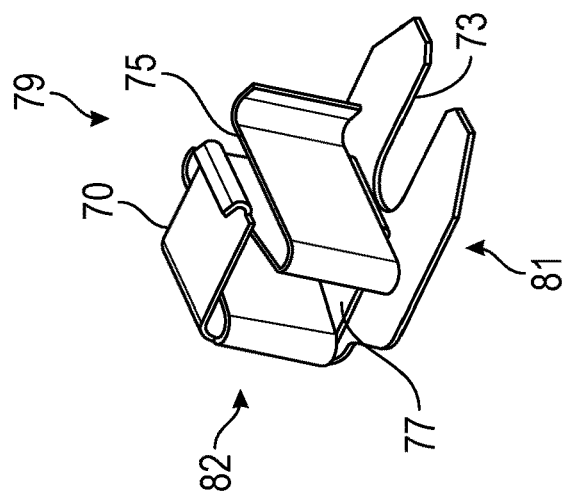
FIG. 21D illustrates a perspective view of the locking member used in the safety needle device of FIG. 21A.
Figure 21C:
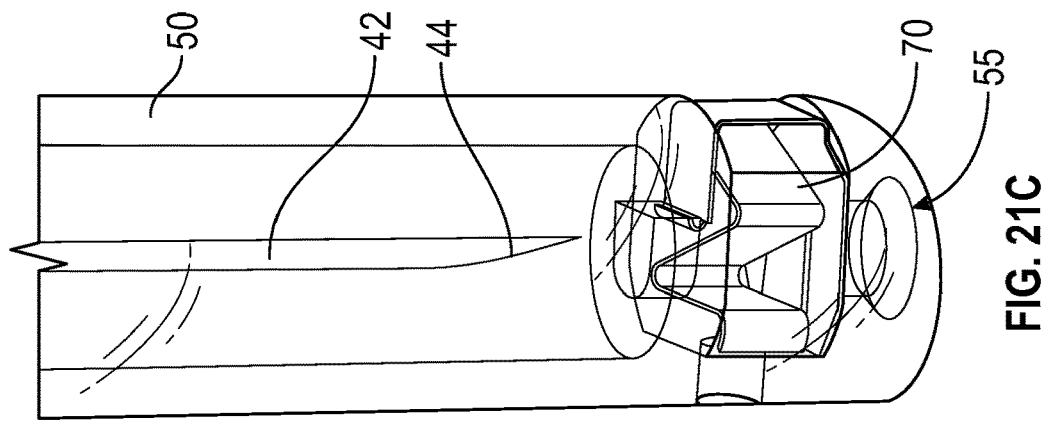
FIG. 21C illustrates a perspective view of the safety needle device of FIG. 21A with the sleeve in an extended and locked position.
Figure 21B:
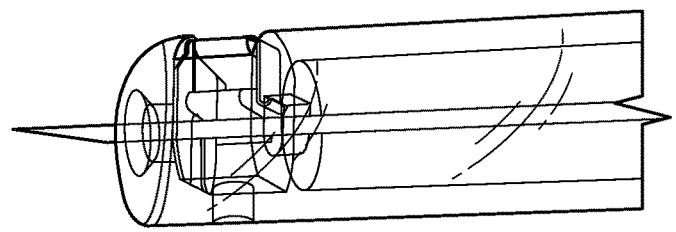
FIG. 21B illustrates a perspective view of the safety needle device of FIG. 21A with the sleeve in an initial position.
Figure 21A:
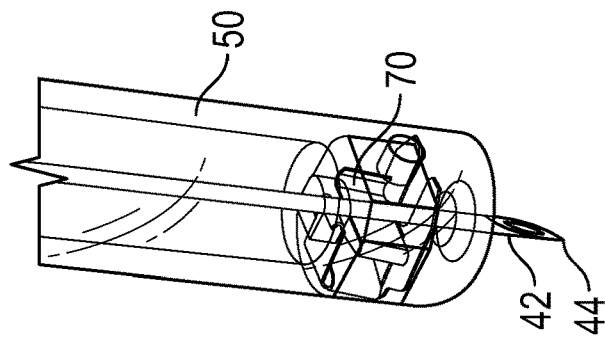
FIG. 21A illustrates a perspective view of a safety needle device according to an alternate embodiment having a locking member with a U-shaped clip and a slot to nest the needle cannula with sleeve in an initial position.
Figure 21E:
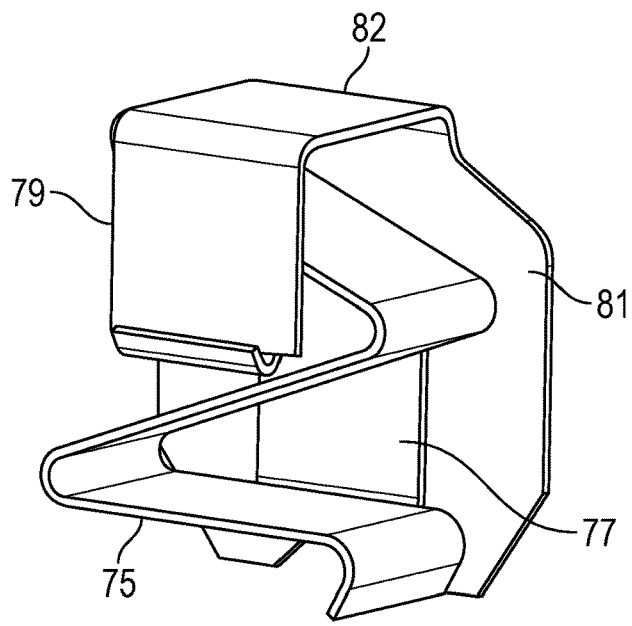
FIG. 21E illustrates a perspective view of the locking member used in the safety needle device of FIG. 21A.
Figure 21F:
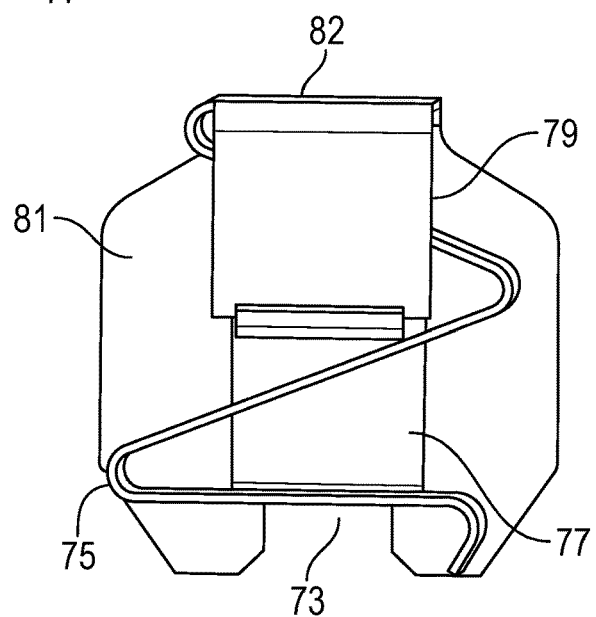
FIG. 21F illustrates a perspective view of the locking member used in the safety needle device of FIG. 21A.
Figure 21G:
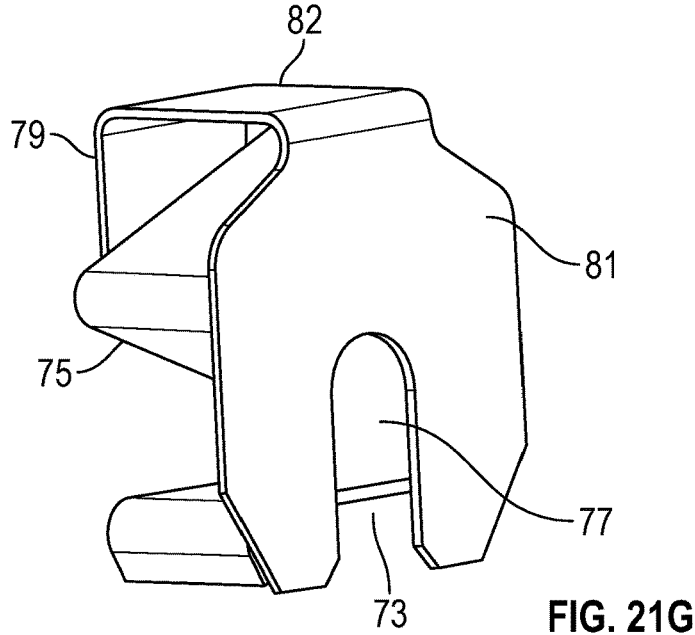
FIG. 21G illustrates a perspective view of the locking member used in the safety needle device of FIG. 21A.

FIGS. 21A-C show an alternate embodiment including a locking member 70 in the form of a spring clip, which has an overall three-dimensional U-shape or L-shape, including a proximal leg 79, a lateral leg 82 and a distal leg 81. As best shown in FIGS. 21D-G, the locking member 70 includes a slot 73 sized and configured to allow a needle cannula 42 to nest therein when the sheath or sleeve 50 is in the initial position and the distal tip 44 of the needle cannula 42 is exposed. The needle cannula 42 slides in the slot 73 while the needle cannula 42 is inserted into a subject or a patient, and the sheath or sleeve 50 moves in a proximal direction as the sheath or sleeve 50 end face contacts the patient's or subject's skin. When the needle cannula 42 is removed from the subject or patient, and the sheath or sleeve 50 moves in a distal direction, the needle cannula 42 slides in the slot 73. The slot 73 is located within the distal leg 81, and a biasing member 75 extends from the lateral leg 82. The biasing member 75 can include a flat spring, a tong spring or a double loop tong spring as shown in FIGS. 21D-G. A gate 77 in the form of a flat sheet protrudes from the biasing member 75. In the initial position, the biasing member 75 rests against the body of the needle cannula 42 to keep gate 77 out of alignment with aperture 55 of sleeve 50 and the slot 73 of the of the locking member 70. In the retracted state, the biasing member 75 rides along the needle cannula 42. After the device is activated, the retractable sleeve 50 moves forward to allow the retractable sleeve 50 and the gate 77 of biasing member 75 to extend past the distal tip 44 of needle cannula 42 which allows stored energy in the compressed flat spring to be released such that the gate 77 covers the slot 73 thereby passively locking out the safety needle device 10 and preventing needle stick injury to the practitioner. The locking member 70 in the form of a U-shaped clip inhibits reuse of the safety needle device 10 by inhibiting further translational movement of the retractable sleeve 50 within the housing body 23 by covering the distal tip 44 of the needle cannula 42 in the extended position. Needle cannula 42 is obscured from view when the retractable sleeve is in the extended position. In this way, the device is a single-use passive safety needle device, as the sleeve 50 automatically covers the distal end of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action.

FIGS. 22A-F show an alternate embodiment with a tether 30 having a hook-shaped portion that prevents the one or more protrusions 52c, 52d from rotating prior to retractable sleeve 50 advancement. In one or more embodiments, the retractable sleeve 50 has one or more protrusions 52c in form of a stabilization bar that interacts with a slot in the housing to rotationally key the sleeve 50 and housing 20. One or more protrusions engage the tether 30 and activate the safety needle device by causing the tether to rotate relative to the housing thereby releasing the tether from the housing. In one or more embodiments, the enlarged first guide path 31 may comprise a branch defining a hook-shaped portion that engages the one or more protrusions and resists relative rotation of the tether and the sleeve until the sleeve is retracted. The one or more protrusions may comprise a single radially extending protrusion having a first portion having a first height and a second portion extending laterally from the first portion, the second portion may have a second height that is less than the first height, and the second portion may have a surface that nests in the hook-shaped portion. In this way, the device is a single-use passive safety needle device, as the sleeve 50 automatically covers the distal end of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action.

Figure 23:
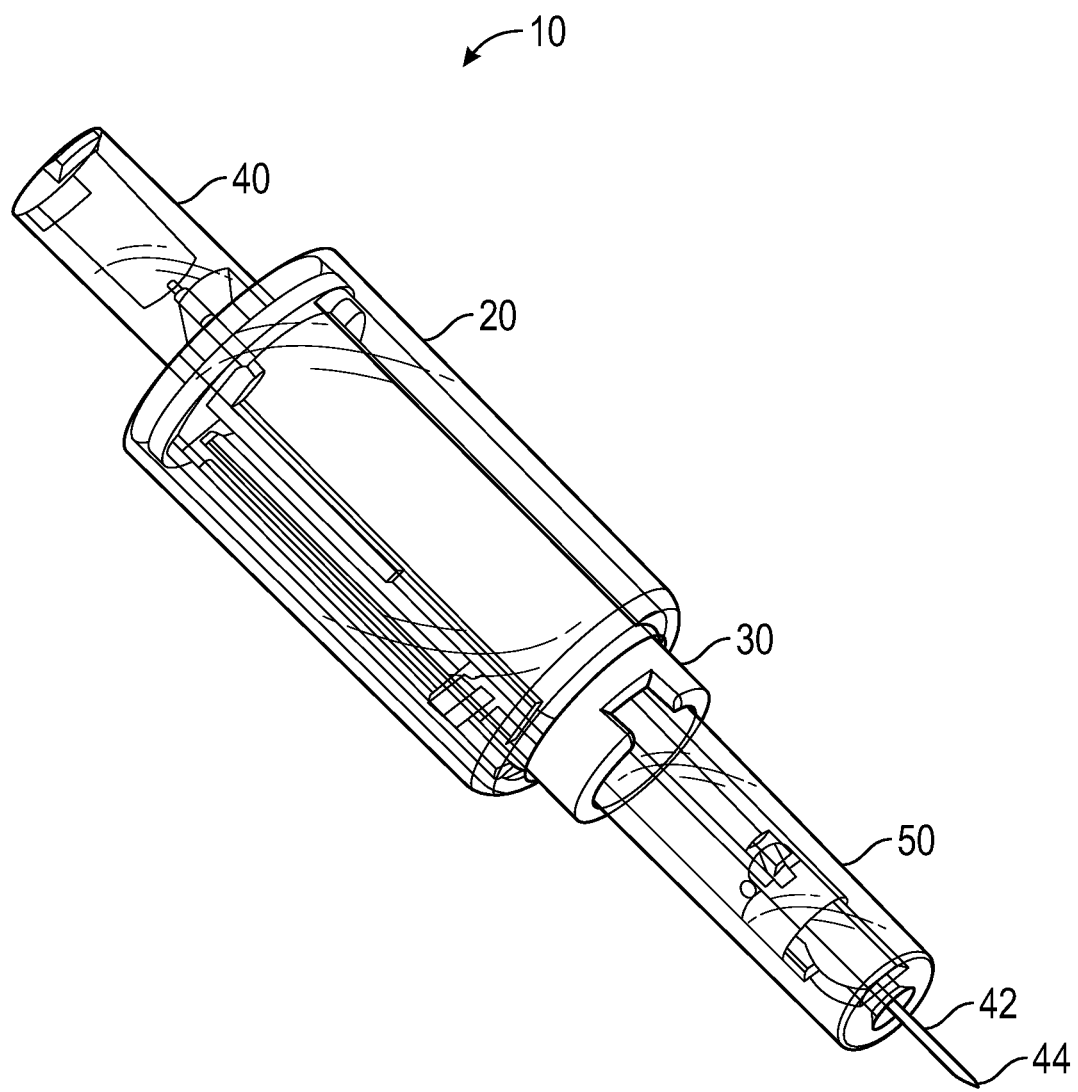
FIG. 23 illustrates a perspective view of a safety needle device according to an alternate embodiment.

As shown in FIG. 23, one or more embodiments include an anti-fire feature. In one embodiment, the slot in the tether interfaces with one or more rib, tab or bar disposed in a cap or hard package so that the safety needle device 10 does not "mis-fire" in transit or storage. Any suitable caps or packaging comprising a safety feature may be used in conjunction with the safety needle device disclosed herein.

Figure 24C:
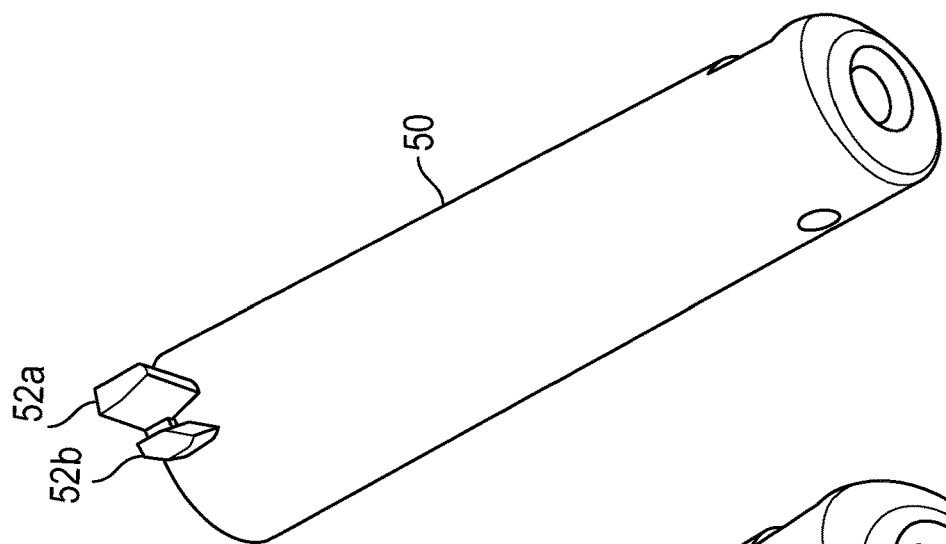
FIG. 24C illustrates a perspective view of a sleeve of a safety needle device according to an alternate embodiment showing an alternate protrusion configuration.
Figure 24B:
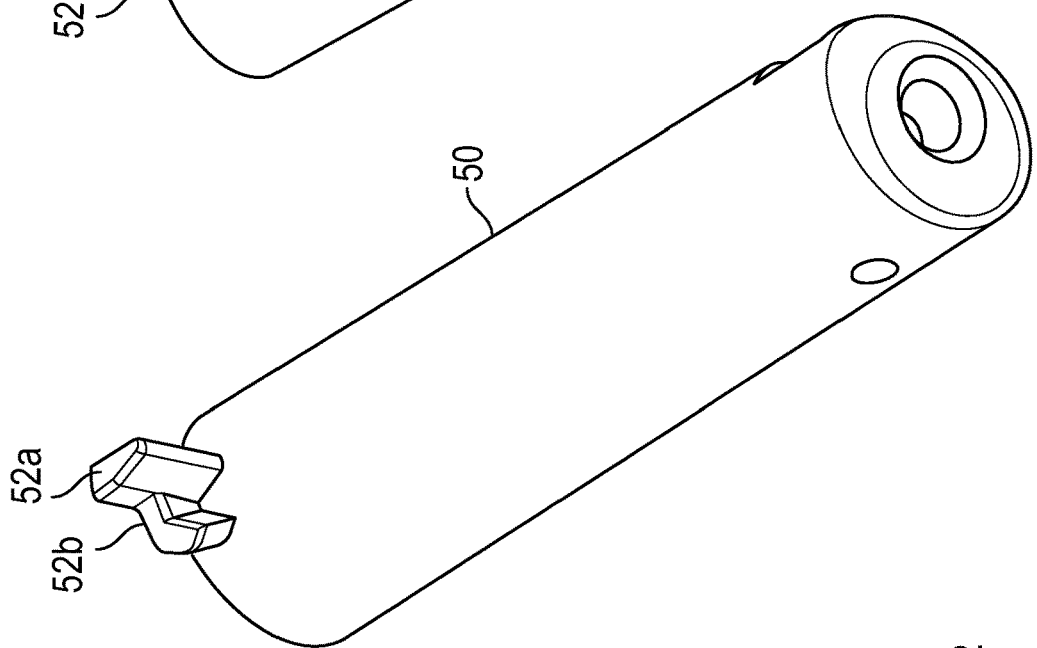
FIG. 24B illustrates a perspective view of a sleeve of a safety needle device according to an alternate embodiment showing an alternate protrusion configuration.
Figure 24A:
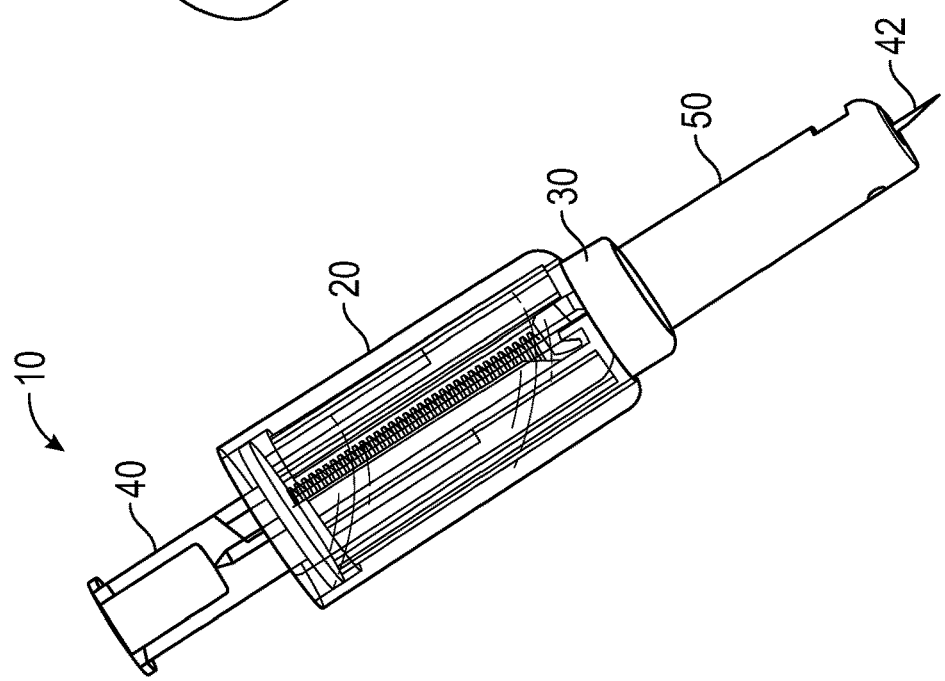
FIG. 24A illustrates a perspective view of a safety needle device according to an alternate embodiment having a retractable sleeve.

FIGS. 24A-C illustrate a perspective view of a safety needle device according to an alternate embodiment having a retractable sleeve 50 with alternative protrusion configurations. As shown in FIG. 24C, an embodiment of the retractable sleeve has separate one or more protrusions 52a, 52b. As shown in FIG. 24b, an alternate embodiment of the retractable sleeve has one or more protrusions 52a, 52b which are connected, joined or integral.

In one or more embodiments, one or more protrusions are disposed on the retractable sleeve to key the retractable sleeve to the housing. The one or more protrusions allow the retractable sleeve to move in and out of the housing but prevent rotation of the retractable sleeve relative to the housing.

In one or more embodiments, one or more protrusions reduce wobbliness between the housing and retractable sleeve, as well as, guide the retractable sleeve from an initial position in the enlarged first guide path of the tether to a second position in the narrowed second guide path of the tether.

In one or more embodiments, the one or more protrusions are in the shape of a T-Bar. The T-shape at the end of the one or more protrusions helps to reduce wobbliness between the housing and retractable sleeve by adding additional guidance and support.

Upon movement of the retractable sleeve in the proximal direction, the T-shaped one or more protrusions move along from the initial position in the enlarged first guide path of the tether to a second position in the narrowed second guide path of the tether that causes the tether to rotate.

In one or more alternate embodiments, the device includes one or more protrusions and one or more pegs on the retractable sleeve that engages with the rotating tether but does not engage with the housing. The one or more pegs activate the device. Upon movement of the retractable sleeve in the proximal direction, the one or more pegs move along a path that causes the tether to rotate while the sleeve is held rotationally fixed by a separate one or more protrusions moving the tether from a first position to a second position. The one or more pegs can be located at any orientation (0-360 degrees) relative to the stabilization feature including but not limited to 0 degrees (same feature), 180 degrees, side by side, or separated by only a few degrees.

In one or more alternative embodiments, the one or more protrusions are in the shape of a dovetail.

Stroke length is the sum of needle cannula length and retractable sleeve 50 length for lock-out travel. The distance between distal end of retractable sleeve 50 and distal tip 44 of needle cannula 42 is a stack-up of tolerances and safety margin to insure NSI is prevented following use.

In one or more embodiments, overall length of the safety needle device may be reduced when the spring element is allowed to collapse inside both the retractable sleeve 50 and housing 20. Thus reducing overall length by the solid height and subsequently lowering forces applied to a patient's skin.

In one or more embodiments, the safety needle device can include a cap that is removably coupled to the housing to reduce or prevent contamination of the needle cannula during shipping and storage of the safety needle device. The cap is generally kept in the closed position until just prior to an injection and/or aspiration procedure, at which time the cap is removed from the housing. In some embodiments, cap may be configured to assist in properly drawing a dose from a vial.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A safety needle device, comprising:
a hub configured to couple to a syringe;
a needle cannula having a proximal end attached to the hub and a distal tip;
a housing having a proximal end, a distal end including a shelf, and a housing body having a length, the hub disposed on the proximal end of the housing;
a tether having a length, the tether movably disposed in the housing, the tether having one or more ribs extending radially from the tether along the length of the tether that interact with one or more guide tracks disposed on an inner surface and along the length of the housing body and the tether further having a slot with an enlarged first guide path and a narrowed second guide path extending distally from the enlarged first guide path;
a retractable sleeve slidably disposed in the tether, the retractable sleeve having one or more protrusions to slidably engage the slot, the retractable sleeve configured to move between an initial position, a retracted position and an extended position with respect to the housing, wherein in the initial position, the tether is constrained within the housing and the distal tip of the needle cannula is partially exposed, in the retracted position, the needle cannula is further exposed, and in the extended position upon activation of the safety needle device causing rotation of the tether from an initial position to a second position and causing axial movement of the tether, and the retractable sleeve fully covers the distal tip of the needle cannula when the one or more ribs no longer constrain the tether and the tether has slidably extended from the sleeve;
a locking member disposed in the retractable sleeve, the locking member configured to cover the distal tip of the needle cannula when the retractable sleeve is in the extended position; and a spring element to bias the retractable sleeve from the retracted position to the extended position.

2. The safety needle device of claim 1, wherein proximal movement of the retractable sleeve from the initial position causes the one or more protrusions of the retractable sleeve to rotate the tether and move the one or more protrusions to move from the enlarged first guide path on the tether to the narrowed second guide path on the tether.

3. The safety needle device of claim 2, wherein the tether rotates with respect to the housing during the proximal movement of the retractable sleeve from the initial position.

4. The safety needle device of claim 3, wherein the one or more protrusions move from the enlarged first guide path, contact a ramping surface and then move to the narrowed second guide path.

5. The safety needle device of claim 1, wherein the tether comprises a first end attached to the housing body and a second end attached to the retractable sleeve.

6. The safety needle device of claim 1, wherein the enlarged first guide path of the tether intersects the narrowed second guide path of the tether.

7. The safety needle device of claim 1, wherein the narrowed second guide path is generally parallel to a central axis and extends along the tether.

8. The safety needle device of claim 1, wherein the enlarged first guide path comprises an angle, curvature or taper relative to a central axis.

9. The safety needle device of claim 8, wherein the angle, curvature or taper of the enlarged first guide path allows the one or more protrusions to rotate the tether from the enlarged first guide path to the narrowed second guide path.

10. The safety needle device of claim 1, wherein the one or more protrusions comprise a first protrusion of a first length "L1" and a second protrusion having a second length less than "L2".

11. The safety needle device of claim 10, wherein the first protrusion is adjacent to the second protrusion.

12. The safety needle device of claim 10, wherein the first protrusion is located 90° to the second protrusion.

13. The safety needle device of claim 10, wherein the first protrusion is located 180° to the second protrusion.

14. The safety needle device of claim 10, wherein the first protrusion is T-shaped.

15. The safety needle device of claim 1, wherein movement of the retractable sleeve from the retracted position to the extended position engages the locking member to the distal tip of the needle cannula.

16. The safety needle device of claim 1, wherein the locking member inhibits reuse of the safety needle device by inhibiting translation of the retractable sleeve.

17. The safety needle device of claim 1, wherein the locking member comprises a gate.

18. The safety needle device of claim 17, further comprising a U-shaped clip with a slot to nest the needle cannula.

19. The safety needle device of claim 18, wherein the gate is attached to a flat spring attached to the clip.

20. The safety needle device of claim 1, wherein the spring element is a coil spring.

21. The safety needle device of claim 1, wherein the one or more protrusions comprise a protrusion radially extending from a proximal portion of the retractable sleeve.

22. The safety needle device of claim 1, wherein the one or more protrusions comprise a first protrusion radially extending from a proximal portion of the retractable sleeve and having a height and a second protrusion radially extending from the proximal portion of the retractable sleeve and having a height, the height of the first protrusion being greater than the height of the second protrusion.

23. The safety needle device of claim 22, wherein the second protrusion contacts the enlarged first guide path when the retractable sleeve is in the initial position and rotates the tether when the retractable sleeve is proximally moved toward the retracted position.

24. The safety needle device of claim 1, wherein the one or more protrusions comprises a single radially extending protrusion having a first portion having a first height and a second portion extending laterally from the first portion, the second portion having a second height that is less than the first height.

25. The safety needle device of claim 24, wherein the second portion contacts the slot when the retractable sleeve is in the initial position and rotates the tether when the retractable sleeve is moved toward the retracted position.

26. The safety needle device of claim 1, wherein the slot in the tether includes a transition region between the enlarged first guide path and the narrowed second guide path, the transition region including an angled surface that uses the one or more protrusions to rotate the tether to the narrowed second guide path from the enlarged first guide path.

27. The safety needle device of claim 1, wherein the enlarged first guide path comprises a branch defining a hook-shaped portion that engages the one or more protrusions and resists relative rotation of the tether and the retractable sleeve until the retractable sleeve is retracted.

28. The safety needle device of claim 27, wherein the one or more protrusions comprises a single radially extending protrusion having a first portion having a first height and a second portion extending laterally from the first portion, the second portion having a second height that is less than the first height, and the second portion having a surface that nests in the hook-shaped portion.

29. The safety needle device of claim 1, wherein the safety needle device is a single-use passive safety needle device, wherein the retractable sleeve automatically covers a distal end of the needle cannula after a patient has been injected and the needle cannula has been removed from the patient.

30. The safety needle device of claim 29, wherein a practitioner or user of the safety needle device does not have to activate the retractable sleeve by pressing a button on the safety needle device or twisting the safety needle device.

* * * * *